(12) United States Patent
Brinkley et al.

(10) Patent No.: US 10,561,178 B2
(45) Date of Patent: Feb. 18, 2020

(54) SEALED CARTRIDGE FOR AN AEROSOL DELIVERY DEVICE AND RELATED ASSEMBLY METHOD

(71) Applicant: RAI Strategic Holdings, Inc., Winston-Salem, NC (US)

(72) Inventors: Paul Andrew Brinkley, Winston-Salem, NC (US); Jack Gray Flinchum, Jr., Clemmons, NC (US); Timothy Brian Nestor, Advance, NC (US); Grady Lance Dooly, Winston-Salem, NC (US); Steven Lee Alderman, Lewisville, NC (US); Frederic Philippe Ampolini, Winston-Salem, NC (US); John DePiano, Burlington, MA (US); David Smith, Needham, MA (US); Frank S. Silveira, Wilmington, MA (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 0 days.

(21) Appl. No.: 16/379,465

(22) Filed: Apr. 9, 2019

(65) Prior Publication Data
US 2019/0230995 A1 Aug. 1, 2019

Related U.S. Application Data

(63) Continuation of application No. 15/938,723, filed on Mar. 28, 2018, now Pat. No. 10,292,434, which is a
(Continued)

(51) Int. Cl.
*A24F 47/00* (2006.01)
*F22B 1/28* (2006.01)
(Continued)

(52) U.S. Cl.
CPC ......... *A24F 47/008* (2013.01); *A61M 11/042* (2014.02); *A61M 15/06* (2013.01);
(Continued)

(58) Field of Classification Search
CPC .................................................. A24F 47/008
See application file for complete search history.

(56) References Cited

U.S. PATENT DOCUMENTS

| 1,771,366 | A | 7/1930 | Wyss et al. |
| 2,057,353 | A | 10/1936 | Whittemore, Jr. |

(Continued)

FOREIGN PATENT DOCUMENTS

| AU | 276250 | 7/1965 |
| CA | 2 641 869 | 5/2010 |

(Continued)

OTHER PUBLICATIONS

International Search Report and Written Opinion of the International Searching Authority for corresponding International Application No. PCT/US2015/031374 dated Aug. 24, 2015.

(Continued)

*Primary Examiner* — Eric Yaary
(74) *Attorney, Agent, or Firm* — Womble Bond Dickinson (US) LLP

(57) ABSTRACT

The present disclosure relates to an aerosol delivery device. The aerosol delivery device may include a control body and a cartridge. The cartridge may include a base, a flow director, an outer body, a reservoir substrate, an outer body, and a mouthpiece. Heating elements may be molded into the flow director. The flow director may be welded to the base and the outer body, or the base and the flow director may include deformable ribs that engage the outer body. The flow director and the outer body may cooperatively define a reservoir compartment in which the reservoir substrate and (Continued)

Figure 1:
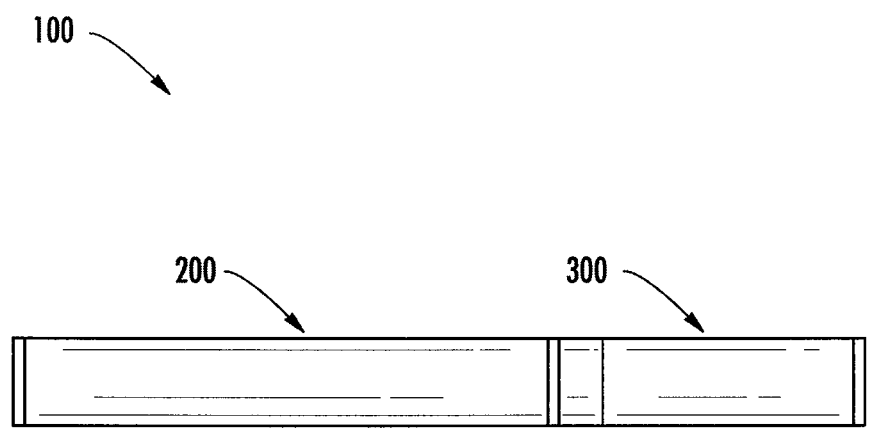

the atomizer are received. The flow director and the base may define an electronics compartment in which an electronic control component is received. A related assembly method is also provided.

18 Claims, 20 Drawing Sheets

Related U.S. Application Data continuation of application No. 14/286,552, filed on May 23, 2014, now Pat. No. 9,955,726.

(51) Int. Cl.
   *H05B 1/02* (2006.01)
   *H05B 3/40* (2006.01)
   *A61M 11/04* (2006.01)
   *A61M 15/06* (2006.01)

(52) U.S. Cl.
   CPC ........... *F22B 1/284* (2013.01); *H05B 1/0297* (2013.01); *H05B 3/40* (2013.01); *A61M 2205/505* (2013.01); *A61M 2205/581* (2013.01); *A61M 2205/583* (2013.01)

(56) References Cited

U.S. PATENT DOCUMENTS

| | | |
|---|---|---|
| 2,104,266 A | 1/1938 | McCormick |
| 3,200,819 A | 8/1965 | Gilbert |
| 4,284,089 A | 8/1981 | Ray |
| 4,303,083 A | 12/1981 | Burruss, Jr. |
| 4,735,217 A | 4/1988 | Gerth et al. |
| 4,848,374 A | 7/1989 | Chard et al. |
| 4,907,606 A | 3/1990 | Lilja et al. |
| 4,922,901 A | 5/1990 | Brooks et al. |
| 4,945,931 A | 8/1990 | Gori |
| 4,947,874 A | 8/1990 | Brooks et al. |
| 4,947,875 A | 8/1990 | Brooks et al. |
| 4,986,286 A | 1/1991 | Roberts et al. |
| 5,019,122 A | 5/1991 | Clearman |
| 5,042,510 A | 8/1991 | Curtiss et al. |
| 5,060,671 A | 10/1991 | Counts et al. |
| 5,093,894 A | 3/1992 | Deevi et al. |
| 5,144,962 A | 8/1992 | Counts et al. |
| 5,249,586 A | 10/1993 | Morgan et al. |
| 5,261,424 A | 11/1993 | Sprinkel, Jr. |
| 5,322,075 A | 6/1994 | Deevi et al. |
| 5,353,813 A | 10/1994 | Deevi et al. |
| 5,369,723 A | 11/1994 | Counts et al. |
| 5,372,148 A | 12/1994 | McCafferty et al. |
| 5,388,574 A | 2/1995 | Ingebrethsen et al. |
| 5,408,574 A | 4/1995 | Deevi et al. |
| 5,468,936 A | 11/1995 | Deevi et al. |
| 5,498,850 A | 3/1996 | Das |
| 5,515,842 A | 5/1996 | Ramseyer et al. |
| 5,530,225 A | 6/1996 | Hajaligol |
| 5,564,442 A | 10/1996 | MacDonald et al. |
| 5,649,554 A | 7/1997 | Sprinkel et al. |
| 5,666,977 A | 9/1997 | Higgins et al. |
| 5,687,746 A | 11/1997 | Rose et al. |
| 5,726,421 A | 3/1998 | Fleischhauer et al. |
| 5,727,571 A | 3/1998 | Meiring et al. |
| 5,799,663 A | 9/1998 | Gross et al. |
| 5,819,756 A | 10/1998 | Mielordt |
| 5,865,185 A | 2/1999 | Collins et al. |
| 5,865,186 A | 2/1999 | Volsey, II |
| 5,878,752 A | 3/1999 | Adams et al. |
| 5,894,841 A | 4/1999 | Voges |
| 5,934,289 A | 8/1999 | Watkins et al. |
| 5,937,140 A | 8/1999 | Leonard et al. |
| 5,954,979 A | 9/1999 | Counts et al. |
| 5,967,148 A | 10/1999 | Harris et al. |
| 6,040,560 A | 3/2000 | Fleischhauer et al. |
| 6,053,176 A | 4/2000 | Adams et al. |
| 6,089,857 A | 7/2000 | Matsuura et al. |
| 6,095,153 A | 8/2000 | Kessler et al. |
| 6,125,853 A | 10/2000 | Susa et al. |
| 6,155,268 A | 12/2000 | Takeuchi |
| 6,164,287 A | 12/2000 | White |
| 6,196,218 B1 | 3/2001 | Voges |
| 6,196,219 B1 | 3/2001 | Hess et al. |
| 6,601,776 B1 | 8/2003 | Oljaca et al. |
| 6,615,840 B1 | 9/2003 | Fournier et al. |
| 6,688,313 B2 | 2/2004 | Wrenn et al. |
| 6,772,756 B2 | 8/2004 | Shayan |
| 6,803,545 B2 | 10/2004 | Blake et al. |
| 6,854,461 B2 | 2/2005 | Nichols |
| 6,854,470 B1 | 2/2005 | Pu |
| 7,117,867 B2 | 10/2006 | Cox et al. |
| 7,293,565 B2 | 11/2007 | Griffin et al. |
| 7,513,253 B2 | 4/2009 | Kobayashi et al. |
| 7,775,459 B2 | 8/2010 | Martens, III et al. |
| 7,832,410 B2 | 11/2010 | Hon |
| 7,845,359 B2 | 12/2010 | Montaser |
| 7,896,006 B2 | 3/2011 | Hamano et al. |
| 8,127,772 B2 | 3/2012 | Montaser |
| 8,314,591 B2 | 11/2012 | Terry et al. |
| 8,365,742 B2 | 2/2013 | Hon |
| 8,402,976 B2 | 3/2013 | Fernando et al. |
| 8,499,766 B1 | 8/2013 | Newton |
| 8,528,569 B1 | 9/2013 | Newton |
| 8,550,069 B2 | 10/2013 | Alelov |
| 9,408,416 B2 | 8/2016 | Monsees et al. |
| 9,549,573 B2 | 1/2017 | Monsees et al. |
| 10,045,567 B2 | 8/2018 | Monsees et al. |
| 10,045,568 B2 | 8/2018 | Monsees et al. |
| 10,058,129 B2 | 8/2018 | Monsees et al. |
| 10,058,130 B2 | 8/2018 | Monsees et al. |
| 10,070,669 B2 | 9/2018 | Monsees et al. |
| 10,076,139 B2 | 9/2018 | Monsees et al. |
| 10,111,470 B2 | 10/2018 | Monsees et al. |
| 10,117,465 B2 | 11/2018 | Monsees et al. |
| 10,117,466 B2 | 11/2018 | Monsees et al. |
| 10,159,282 B2 | 12/2018 | Monsees et al. |
| 10,201,190 B2 | 2/2019 | Monsees et al. |
| 10,264,823 B2 | 4/2019 | Monsees et al. |
| 2002/0146242 A1 | 10/2002 | Vieira |
| 2003/0226837 A1 | 12/2003 | Blake et al. |
| 2004/0118401 A1 | 6/2004 | Smith et al. |
| 2004/0129280 A1 | 7/2004 | Woodson et al. |
| 2004/0200488 A1 | 10/2004 | Felter et al. |
| 2004/0226568 A1 | 11/2004 | Takeuchi et al. |
| 2005/0016550 A1 | 1/2005 | Katase |
| 2006/0016453 A1 | 1/2006 | Kim |
| 2006/0196518 A1 | 9/2006 | Hon |
| 2007/0074734 A1 | 4/2007 | Braunshteyn et al. |
| 2007/0102013 A1 | 5/2007 | Adams et al. |
| 2007/0215167 A1 | 9/2007 | Crooks et al. |
| 2007/0283972 A1 | 12/2007 | Monsees et al. |
| 2008/0085103 A1 | 4/2008 | Beland et al. |
| 2008/0092912 A1 | 4/2008 | Robinson et al. |
| 2008/0257367 A1 | 10/2008 | Paterno et al. |
| 2008/0276947 A1 | 11/2008 | Martzel |
| 2008/0302374 A1 | 12/2008 | Wengert et al. |
| 2009/0095311 A1 | 4/2009 | Hon |
| 2009/0095312 A1 | 4/2009 | Herbrich et al. |
| 2009/0126745 A1 | 5/2009 | Hon |
| 2009/0151717 A1 | 6/2009 | Bowen et al. |
| 2009/0188490 A1 | 7/2009 | Hon |
| 2009/0230117 A1 | 9/2009 | Fernando et al. |
| 2009/0272379 A1 | 11/2009 | Thorens et al. |
| 2009/0283103 A1 | 11/2009 | Nielsen et al. |
| 2009/0320863 A1 | 12/2009 | Fernando et al. |
| 2010/0043809 A1 | 2/2010 | Magnon |
| 2010/0083959 A1 | 4/2010 | Siller |
| 2010/0200006 A1 | 8/2010 | Robinson et al. |
| 2010/0229881 A1 | 9/2010 | Hearn |
| 2010/0242974 A1 | 9/2010 | Pan |
| 2010/0307518 A1 | 12/2010 | Wang |
| 2010/0313901 A1 | 12/2010 | Fernando et al. |
| 2011/0005535 A1 | 1/2011 | Xiu |

(56) References Cited

U.S. PATENT DOCUMENTS

| | | |
|---|---|---|
| 2011/0011396 A1 | 1/2011 | Fang |
| 2011/0036363 A1 | 2/2011 | Urtsev et al. |
| 2011/0036365 A1 | 2/2011 | Chong et al. |
| 2011/0094523 A1 | 4/2011 | Thorens et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0168194 A1 | 7/2011 | Hon |
| 2011/0265806 A1 | 11/2011 | Alarcon et al. |
| 2011/0309157 A1 | 12/2011 | Yang et al. |
| 2012/0042885 A1 | 2/2012 | Stone et al. |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0199663 A1 | 8/2012 | Qiu |
| 2012/0227752 A1 | 9/2012 | Alelov |
| 2012/0227753 A1 | 9/2012 | Newton |
| 2012/0231464 A1 | 9/2012 | Yu et al. |
| 2012/0260927 A1 | 10/2012 | Liu |
| 2012/0279512 A1 | 11/2012 | Hon |
| 2012/0318882 A1 | 12/2012 | Abehasera |
| 2013/0037041 A1 | 2/2013 | Worm et al. |
| 2013/0042865 A1 | 2/2013 | Monsees et al. |
| 2013/0056013 A1 | 3/2013 | Terry et al. |
| 2013/0081625 A1 | 4/2013 | Rustad et al. |
| 2013/0081642 A1 | 4/2013 | Safari |
| 2013/0133675 A1 | 5/2013 | Shinozaki et al. |
| 2013/0160764 A1 | 6/2013 | Liu |
| 2013/0192619 A1 | 8/2013 | Tucker et al. |
| 2013/0192620 A1 | 8/2013 | Tucker et al. |
| 2013/0213419 A1 * | 8/2013 | Tucker ................. A24F 47/008 131/328 |
| 2013/0220315 A1 | 8/2013 | Conley et al. |
| 2013/0284192 A1 | 10/2013 | Peleg et al. |
| 2013/0306084 A1 | 11/2013 | Flick |
| 2013/0312742 A1 | 11/2013 | Monsees et al. |
| 2013/0312776 A1 | 11/2013 | Newton |
| 2013/0319439 A1 | 12/2013 | Gorelick et al. |
| 2013/0340750 A1 | 12/2013 | Thorens et al. |
| 2013/0340775 A1 | 12/2013 | Juster et al. |
| 2014/0000638 A1 | 1/2014 | Sebastian et al. |
| 2014/0041655 A1 | 2/2014 | Barron et al. |
| 2014/0060552 A1 | 3/2014 | Cohen |
| 2014/0060554 A1 | 3/2014 | Collett et al. |
| 2014/0060555 A1 | 3/2014 | Chang et al. |
| 2014/0076310 A1 | 3/2014 | Newton |
| 2014/0096781 A1 | 4/2014 | Sears et al. |
| 2014/0096782 A1 | 4/2014 | Ampolini et al. |
| 2014/0109921 A1 | 4/2014 | Chen |
| 2014/0196717 A1 | 7/2014 | Liu |
| 2014/0196734 A1 | 7/2014 | Liu |
| 2014/0332021 A1 | 11/2014 | Li et al. |
| 2014/0345631 A1 | 11/2014 | Bowen et al. |
| 2014/0366898 A1 | 12/2014 | Monsees et al. |
| 2015/0020824 A1 | 1/2015 | Bowen et al. |
| 2015/0040927 A1 | 2/2015 | Li et al. |
| 2015/0090280 A1 | 4/2015 | Chen |
| 2015/0157054 A1 | 6/2015 | Liu |
| 2015/0196058 A1 | 7/2015 | Lord |
| 2015/0201675 A1 | 7/2015 | Lord |
| 2015/0208729 A1 | 7/2015 | Monsees et al. |
| 2016/0157523 A1 | 6/2016 | Liu |
| 2016/0374391 A1 | 12/2016 | Liu |

FOREIGN PATENT DOCUMENTS

| | | |
|---|---|---|
| CA | 2 886 292 | 4/2014 |
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| CN | 203398241 | 1/2014 |
| CN | 203523810 | 4/2014 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 316 286 | 5/2011 |
| GB | 2469850 | 11/2010 |
| WO | WO 1997/48293 | 12/1997 |
| WO | WO 2004/043175 | 5/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2012/072264 | 6/2012 |
| WO | WO 2012/072762 | 6/2012 |
| WO | WO 2012/100523 | 8/2012 |
| WO | WO 2013/089551 | 6/2013 |
| WO | WO 2014/012905 | 1/2014 |
| WO | WO 2014/047869 | 4/2014 |
| WO | WO 2014/071329 | 5/2014 |

OTHER PUBLICATIONS

Russian Office Action; Russian Patent Application No. 2016147203; dated Aug. 17, 2018.

* cited by examiner

SEALED CARTRIDGE FOR AN AEROSOL DELIVERY DEVICE AND RELATED ASSEMBLY METHOD

CROSS-REFERENCE TO RELATED APPLICATIONS

This application is a continuation of U.S. patent application Ser. No. 15/938,723, filed Mar. 28, 2018, which is a continuation of U.S. patent application Ser. No. 14/286,552, filed May 23, 2014, which issued on May 1, 2018, as U.S. Pat. No. 9,955,726, each of which is hereby incorporated by reference in its entirety in this application.

FIELD OF THE DISCLOSURE

The present disclosure relates to aerosol delivery devices, and more particularly, to aerosol delivery devices that include a sealed cartridge. The aerosol delivery device includes an atomizer comprising a heating element configured to heat an aerosol precursor. The aerosol precursor, which may include components made or derived from tobacco or otherwise incorporate tobacco, is heated by the atomizer to produce an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al., U.S. Pat. App. Pub. No. 2013/0255702 to Griffith Jr. et al., U.S. Pat. App. Pub. No. 2014/0000638 to Sebastian et al., U.S. Pat. App. Pub. No. 2014/0060554 to Collett et al., U.S. patent application Ser. No. 13/647,000 to Sears et al., filed Oct. 8, 2012, U.S. patent application Ser. No. 13/826,929 to Ampolini et al., filed Mar. 14, 2013, and U.S. patent application Ser. No. 14/011,992 to Davis et al., filed Aug. 28, 2013, which are incorporated herein by reference in their entirety.

Certain existing embodiments of aerosol delivery devices include a control body and a cartridge. A power source (e.g., a battery) may be positioned in the control body and an aerosol precursor composition may be positioned in the cartridge. However, the aerosol precursor composition may be prone to leak from the cartridge, particularly during filling of the cartridge. Thus, advances with respect to configurations of cartridges for aerosol delivery devices which resist leakage or otherwise improve performance thereof and methods of assembly thereof may be desirable.

BRIEF SUMMARY OF THE DISCLOSURE

The present disclosure relates to aerosol delivery devices which, in certain embodiments, may be characterized as electronic cigarettes. In one aspect a cartridge for an aerosol delivery device is provided. The cartridge may include an outer body, a flow director coupled to the outer body, a base coupled to the flow director, and an atomizer received within the outer body. The flow director and the outer body may define a reservoir compartment and the flow director and the base define an electronics compartment.

In some embodiments the cartridge may further include a reservoir substrate in the reservoir compartment. The reservoir substrate may be partially wrapped around the flow director such that a gap is defined between first and second ends thereof. The reservoir substrate may be at least partially wrapped about the flow director and engaged with a plurality of protrusions defined by the flow director and extending therefrom. The flow director may define a recess. The recess may define a channel between the flow director and the reservoir substrate.

In some embodiments the cartridge may further include at least one heating terminal molded into the flow director and extending to a connector end of the base. The cartridge may additionally include an electronic control component positioned within the electronics compartment and a control component terminal extending from the electronic control component to a connector end of the base. The base may define a deformable rib configured to seal against an inner surface of the outer body. The flow director may define a deformable rib configured to seal against an inner surface of the outer body.

In some embodiments the flow director may be welded to the outer body. The flow director may also be welded to the base. The cartridge may additionally include a one-way valve configured to resist flow of air from the flow director through the base. The one-way valve may be selected from a group consisting of a flap valve and a cross-valve. The one-way valve may be positioned in the electronics compartment. The cartridge may further include a mouthpiece coupled to the outer body at an end thereof opposite from the base. The mouthpiece may define an extension configured to reduce an empty volume within the outer body. A spacer may be positioned between the mouthpiece and the atomizer. The spacer may be configured to reduce an empty volume within the outer body. The mouthpiece may include a lip defining a channel. The lip and the channel may extend around an aperture defined through the mouthpiece.

In an additional aspect a method for assembling a cartridge for an aerosol delivery device is provided. The method may include coupling a base to a flow director such that the flow director and the base define an electronics compartment, positioning an atomizer within an outer body, and coupling the outer body to the flow director such that the outer body and the flow director define a reservoir compartment.

Figure 19:
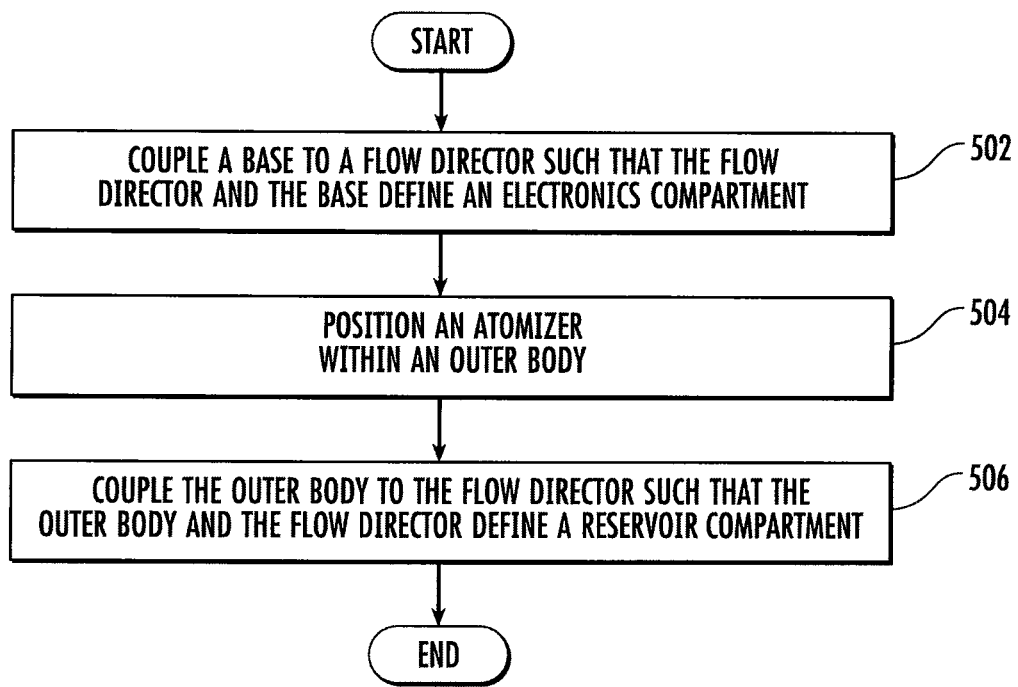
Figure 20:
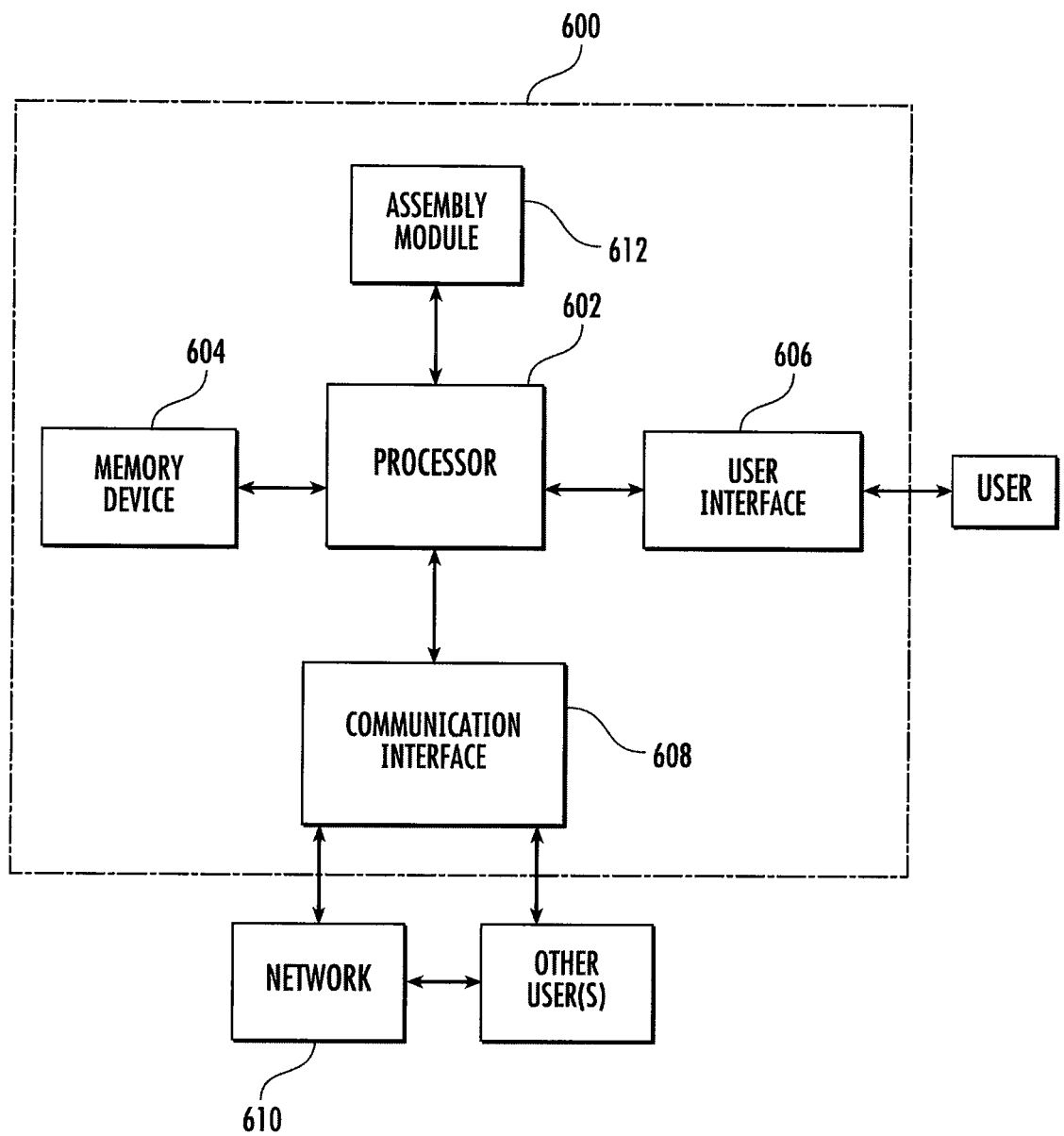

In some embodiments the method may further include wrapping a reservoir substrate configured to store an aerosol precursor composition at least partially about the flow director and positioning the reservoir substrate within the reservoir compartment. Wrapping the reservoir substrate at least partially about the flow director may include engaging the reservoir substrate with a plurality of protrusions defined by the flow director and extending therefrom. Additionally, wrapping the reservoir substrate at least partially about the flow director may include wrapping the reservoir substrate partially about the flow director such that a gap is defined between first and second ends thereof. Wrapping the reservoir substrate at least partially about the flow director may also include forming a channel between the flow director and the reservoir substrate at a cutout defined in the flow director. In some embodiments the method may additionally include molding at least one heating terminal into the flow director. The method may additionally include filling the reservoir substrate with the aerosol precursor composition by directing the aerosol precursor composition into at least one of a gap between first and second ends of the reservoir substrate and a channel between the flow director and the reservoir substrate at a cutout defined in the flow director.

In some embodiments the method may further include positioning an electronic control component in the electronics compartment and connecting a control component terminal to the electronic control component. Coupling the outer body to the flow director may include deforming a deformable rib of the flow director against an inner surface of the outer body. Coupling the outer body to the flow director may include welding the outer body to the flow director. The method may additionally include coupling the outer body to the base. Coupling the outer body to the base may include deforming a deformable rib of the base against an inner surface of the outer body. Coupling the base to the flow director may include welding the base to the flow director. Further, the method may include coupling a one-way valve to the base. The one-way valve may be configured to resist flow of air from the flow director through the base.

In an additional aspect a cartridge for an aerosol delivery device is provided. The cartridge may include an outer body, an atomizer at least partially received within the outer body, a flow director at least partially received within the outer body, and a plurality of heating terminals coupled to the atomizer and extending at least partially though the flow director.

In some embodiments the heating terminals may be molded into the flow director. The cartridge may further include a base. The base may be coupled to at least one of the outer body and the flow director. The flow director and the outer body may define a reservoir compartment and the flow director and the base may define an electronics compartment.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE FIGURES

Having thus described the disclosure in the foregoing general terms, reference will now be made to the accompanying drawings, which are not necessarily drawn to scale, and wherein:

FIG. 1 illustrates a side view of an aerosol delivery device in an assembled configuration, the aerosol delivery device having the general configuration of what can be characterized as an electronic cigarette, and comprising a control body and a cartridge according to an example embodiment of the present disclosure;

FIG. 2 illustrates a side view of the cartridge and a section view through the control body of the aerosol delivery device of FIG. 1 wherein the cartridge is decoupled from the control body according to an example embodiment of the present disclosure;

FIG. 3 illustrates an exploded perspective view of the cartridge of FIG. 1, including a base, a control component terminal, an electronic control component, first and second heating terminals, a flow director, a reservoir substrate, an atomizer, an outer body, a mouthpiece, and a label according to an example embodiment of the present disclosure;

FIG. 4 illustrates a bottom perspective view of a back of the flow director and the first and second heating terminals of FIG. 3 according to an example embodiment of the present disclosure;

FIG. 5 illustrates an opposing top perspective view of a front of the flow director and first and second heating terminals of FIG. 3 according to an example embodiment of the present disclosure;

FIG. 6 illustrates a top perspective view of the base, the electronic control component, and the control component terminal of FIG. 3 according to an example embodiment of the present disclosure;

FIG. 7 illustrates a top perspective view of the assembly of FIG. 6 and further including the heating terminals of FIG. 3 according to an example embodiment of the present disclosure;

FIG. 8 illustrates a bottom perspective view of the assembly of FIG. 7 and further including the flow director of FIG. 3 according to an example embodiment of the present disclosure;

FIG. 9 illustrates a side perspective view of the assembly of FIG. 8 and further including the atomizer of FIG. 3 according to an example embodiment of the present disclosure;

FIG. 10 illustrates the assembly of FIG. 9 and further including the reservoir substrate of FIG. 3 according to an example embodiment of the present disclosure;

FIG. 11 illustrates a partial sectional view through the cartridge of FIG. 2 along line 11-11 according to an embodiment of the present disclosure in which deformable ribs on the base and flow director engage the outer body;

FIG. 12 illustrates a partial sectional view through the cartridge of FIG. 2 along line 11-11 according to an embodiment of the present disclosure in which the flow director is welded to the base and the outer body;

FIG. 13 illustrates a sectional view through the cartridge of FIG. 2 along line 13-13 wherein the outer body is hidden for clarity purposes and wherein the flow director defines recesses according to an example embodiment of the present disclosure;

FIG. 14 illustrates a sectional view through the cartridge of FIG. 2 along line 14-14 according to an example embodiment of the present disclosure;

FIG. 15 illustrates a partial sectional view through the cartridge of FIG. 2 along line 15-15 according to an example embodiment of the present disclosure in which the mouthpiece includes a lip;

FIG. 16 schematically illustrates a sectional view through the cartridge of FIG. 2 along line 14-14 according to an example embodiment of the present disclosure in which the atomizer extends through the flow director;

FIG. 17 illustrates a partial sectional view through the cartridge of FIG. 2 along line 11-11 according to an embodiment of the present disclosure in which deformable ribs on the base and flow director engage the outer body and further including a flap valve;

FIG. 18 illustrates a partial sectional view through the cartridge of FIG. 2 along line 11-11 according to an embodiment of the present disclosure in which the flow director is welded to the base and the outer body and further including a cross valve;

FIG. 19 schematically illustrates a method for assembling a cartridge according to an example embodiment of the present disclosure; and FIG. 20 schematically illustrates a controller according to an example embodiment of the present disclosure.

DETAILED DESCRIPTION OF PREFERRED EMBODIMENTS

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural variations unless the context clearly dictates otherwise.

Aerosol delivery devices according to the present disclosure may use electrical energy to heat a material (preferably without combusting the material to any significant degree) to form an inhalable substance; such articles most preferably being sufficiently compact to be considered "hand-held" devices. An aerosol delivery device may provide some or all of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe, without any substantial degree of combustion of any component of that article or device. The aerosol delivery device may not produce smoke in the sense of the aerosol resulting from by-products of combustion or pyrolysis of tobacco, but rather, that the article or device most preferably yields vapors (including vapors within aerosols that can be considered to be visible aerosols that might be considered to be described as smoke-like) resulting from volatilization or vaporization of certain components of the article or device. In highly preferred embodiments, aerosol delivery devices may incorporate tobacco and/or components derived from tobacco. As such, the aerosol delivery device can be characterized as an electronic smoking article such as an electronic cigarette.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

In use, aerosol delivery devices of the present disclosure may be subjected to many of the physical actions employed by an individual in using a traditional type of smoking article (e.g., a cigarette, cigar or pipe that is employed by lighting and inhaling tobacco). For example, the user of an aerosol delivery device of the present disclosure can hold that article much like a traditional type of smoking article, draw on one end of that article for inhalation of aerosol produced by that article, take puffs at selected intervals of time, etc.

Smoking articles of the present disclosure generally include a number of components provided within an outer shell or body. The overall design of the outer shell or body can vary, and the format or configuration of the outer body that can define the overall size and shape of the smoking article can vary. Typically, an elongated body resembling the shape of a cigarette or cigar can be a formed from a single, unitary shell; or the elongated body can be formed of two or more separable pieces. For example, a smoking article can comprise an elongated shell or body that can be substantially tubular in shape and, as such, resemble the shape of a conventional cigarette or cigar. In one embodiment, all of the components of the smoking article are contained within one outer body or shell. Alternatively, a smoking article can comprise two or more shells that are joined and are separable. For example, a smoking article can possess at one end a control body comprising a shell containing one or more reusable components (e.g., a rechargeable battery and various electronics for controlling the operation of that article), and at the other end and removably attached thereto a shell containing a disposable portion (e.g., a disposable flavor-containing cartridge). More specific formats, configurations and arrangements of components within the single shell type of unit or within a multi-piece separable shell type of unit will be evident in light of the further disclosure provided herein. Additionally, various smoking article designs and component arrangements can be appreciated upon consideration of the commercially available electronic smoking articles, such as those representative products listed in the background art section of the present disclosure.

Aerosol delivery devices of the present disclosure most preferably comprise some combination of a power source (i.e., an electrical power source), at least one control component (e.g., means for actuating, controlling, regulating and/or ceasing power for heat generation, such as by controlling electrical current flow from the power source to other components of the aerosol delivery device), a heater or heat generation component (e.g., an electrical resistance heating element or component commonly referred to as part of an "atomizer"), and an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined air flow path through the article such that aerosol generated can be withdrawn therefrom upon draw). Exemplary formulations for aerosol precursor materials that may be used according to the present disclosure are described in U.S. Pat. Pub. No. 2013/0008457 to Zheng et al. and U.S. Pat. Pub. No. 2013/0213417 to Chong et al., the disclosures of which are incorporated herein by reference in their entirety.

Alignment of the components within the aerosol delivery device of the present disclosure can vary. In specific embodiments, the aerosol precursor composition can be located near an end of the aerosol delivery device which may be configured to be positioned proximal to the mouth of a user so as to maximize aerosol delivery to the user. Other configurations, however, are not excluded. Generally, the heating element can be positioned sufficiently near the aerosol precursor composition so that heat from the heating element can volatilize the aerosol precursor (as well as one or more flavorants, medicaments, or the like that may likewise be provided for delivery to a user) and form an aerosol for delivery to the user. When the heating element heats the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof.

As noted above, the aerosol delivery device may incorporate a battery or other electrical power source (e.g., a capacitor) to provide current flow sufficient to provide various functionalities to the aerosol delivery device, such as powering of a heater, powering of control systems, powering of indicators, and the like. The power source can take on various embodiments. Preferably, the power source is able to deliver sufficient power to rapidly heat the heating element to provide for aerosol formation and power the aerosol delivery device through use for a desired duration of time. The power source preferably is sized to fit conveniently within the aerosol delivery device so that the aerosol delivery device can be easily handled. Additionally, a preferred power source is of a sufficiently light weight to not detract from a desirable smoking experience.

More specific formats, configurations and arrangements of components within the aerosol delivery device of the present disclosure will be evident in light of the further disclosure provided hereinafter. Additionally, the selection of various aerosol delivery device components can be appreciated upon consideration of the commercially available electronic aerosol delivery devices, such as those representative products listed in the background art section of the present disclosure. Further, the arrangement of the components within the aerosol delivery device can also be appreciated upon consideration of the commercially available electronic aerosol delivery devices, such as those representative products listed in the background art section of the present disclosure.

One example embodiment of an aerosol delivery device 100 according to the present disclosure is illustrated in FIG. 1. As illustrated, the aerosol delivery device 100 may include a control body 200 and a cartridge 300. In this regard, FIG. 1 illustrates the control body 200 and the cartridge 300 respectively in an assembled configuration, wherein the control body and the cartridge are coupled to one another. Various mechanisms may connect the control body 200 to the cartridge 300 to result in a threaded engagement, a press-fit engagement, an interference fit, a magnetic engagement, or the like.

The components of the control body 200 and the cartridge 300 may be formed from a variety of materials. For example, plastic (e.g., polycarbonate or acrylonitrile butadiene styrene (ABS)), metal (e.g., stainless steel or aluminum), paperboard, cardboard, ceramic, fiberglass, glass (e.g., a resilient glass), or a graphite composite may be employed to form components of the aerosol delivery device. Various other materials that may be employed in the aerosol delivery device are discussed below in particular reference to certain specified components thereof.

The aerosol delivery device 100 may be substantially rod-like, substantially tubular shaped, or substantially cylindrically shaped in some embodiments when the control body 200 and the cartridge 300 are coupled to one another. In this regard, in some embodiments it may be preferable to provide the aerosol delivery device 100 with a size, shape, and/or configuration resembling a smoking article such as a cigarette or cigar. Thus, in some embodiments the control body 200 and the cartridge 300 may be generally cylindrical and the aerosol delivery device 100 may define an elongated cylindrical configuration as a result of coupling therebetween. Accordingly, the typical size, shape and/or general appearance of the aerosol delivery device 100 may be comparable to commercially available electronic cigarettes.

In some embodiments the control body 200 and the cartridge 300 may define substantially the same longitudinal length. However, in other embodiments the control body 200 and the cartridge 300 may define differing longitudinal lengths. For example, a ratio of a longitudinal length of the cartridge 300 to a longitudinal length of the control body 200 may be from about 2:1 to about 1:2, from about 3:5 to about 5:3, or from about 4:5 to about 5:4. In this regard, in some embodiments the dimensions of the cartridge 300 may be similar to that of a filter element and the dimensions of the control body 200 may be similar to that of a tobacco rod of a traditional cigarette. This configuration may provide adequate room in the control body 200 for an electrical power source, which may be included therein as discussed above and hereinafter.

In one embodiment the control body 200 and the cartridge 300 may be permanently coupled to one another in the configuration illustrated in FIG. 1. Examples of aerosol delivery devices which may be configured to be disposable and/or which may include first and second outer bodies that are configured for permanent coupling are disclosed in U.S. patent application Ser. No. 14/170,838 to Bless et al., filed Feb. 3, 2014, which is incorporated herein by reference in its entirety. However, in another embodiment the control body 200 and the cartridge 300 may be configured to be separable. In this regard, FIG. 2 illustrates the control body 200 and the cartridge 300 in a decoupled configuration, wherein a side view of the cartridge and a sectional view through the control body are provided.

In specific embodiments, one or both of the control body 200 and the cartridge 300 may be referred to as being disposable or as being reusable. For example, the control body 200 may have a replaceable battery or a rechargeable battery and thus may be combined with any type of recharging technology, including connection to a typical alternating current electrical outlet, connection to a car charger (i.e., cigarette lighter receptacle), and connection to a computer, such as through a universal serial bus (USB) cable. Further, in some embodiments the cartridge 300 may comprise a single-use cartridge, as disclosed in U.S. Pat. App. Pub. No. 2014/0060555 to Chang et al., which is incorporated herein by reference in its entirety.

Figure 2:
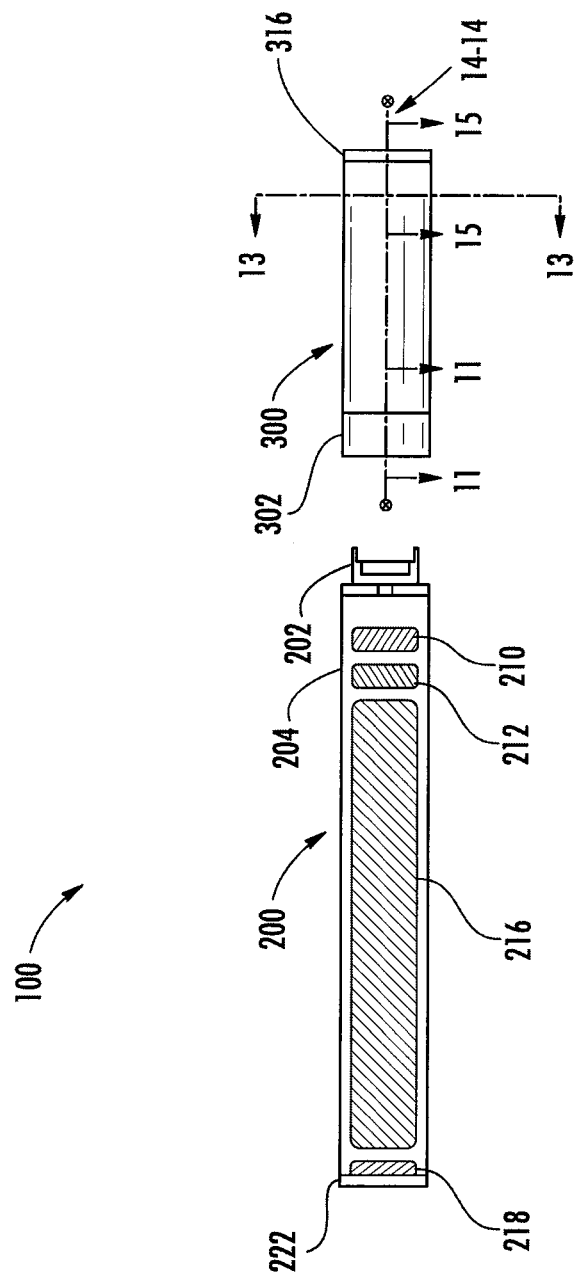

As illustrated in FIG. 2, the control body 200 may comprise a plurality of components. For example, the control body 200 may include a coupler 202, an outer body 204, a flow sensor 210, a control component 212 an electrical power source 216 (e.g., a battery, which may be rechargeable), an indicator 218 (e.g., an LED indicator), and an end cap 222. Various element that may be included in a control body are described in U.S. patent application Ser. No. 14/193,961 to Worm et al., filed Feb. 28, 2014, which is incorporated herein by reference in its entirety.

The various components of an aerosol delivery device according to the present disclosure can be chosen from components described in the art and commercially available. Examples of batteries that can be used according to the disclosure are described in U.S. Pat. App. Pub. No. 2010/

0028766 to Peckerar et al., the disclosure of which is incorporated herein by reference in its entirety.

The aerosol generating piece most preferably incorporates a sensor or detector for control of supply of electric power to the heat generation element when aerosol generation is desired (e.g., upon draw during use). As such, for example, there is provided a manner or method for turning off the power supply to the heat generation element when the aerosol generating piece is not be drawn upon during use, and for turning on the power supply to actuate or trigger the generation of heat by the heat generation element during draw. Additional representative types of sensing or detection mechanisms, structure and configuration thereof, components thereof, and general methods of operation thereof, are described in U.S. Pat. No. 5,261,424 to Sprinkel, Jr.; U.S. Pat. No. 5,372,148 to McCafferty et al.; and PCT WO 2010/003480 by Flick; which are incorporated herein by reference.

The aerosol generating piece most preferably incorporates a control mechanism for controlling the amount of electric power to the heat generation element during draw. Representative types of electronic components, structure and configuration thereof, features thereof, and general methods of operation thereof, are described in U.S. Pat. No. 4,735,217 to Gerth et al.; U.S. Pat. No. 4,947,874 to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al. and U.S. Pat. No. 8,205,622 to Pan; U.S. Pat. Pub. Nos. 2009/0230117 to Fernando et al. and 2014/0060554 to Collet et al.; and U.S. patent application Ser. No. 13/837,542, filed Mar. 15, 2013, to Ampolini et al. and Ser. No. 14/209,191, filed Mar. 13, 2014, to Henry et al.; which are incorporated herein by reference.

Representative types of substrates, reservoirs or other components for supporting the aerosol precursor are described in U.S. Pat. No. 8,528,569 to Newton; and U.S. patent application Ser. No. 13/802,950, filed Mar. 15, 2013, to Chapman et al.; Ser. No. 14/011,192, filed Aug. 28, 2013, to Davis et al. and Ser. No. 14/170,838, filed Feb. 3, 2014, to Bless et al.; which are incorporated herein by reference. Additionally, various wicking materials, and the configuration and operation of those wicking materials within certain types of electronic cigarettes, are set forth in U.S. patent application Ser. No. 13/754,324, filed Jan. 30, 2013, to Sears et al.; which is incorporated herein by reference. A variety of the materials disclosed by the foregoing documents may be incorporated into the present devices in various embodiments, and all of the foregoing disclosures are incorporated herein by reference in their entireties.

Figure 3:
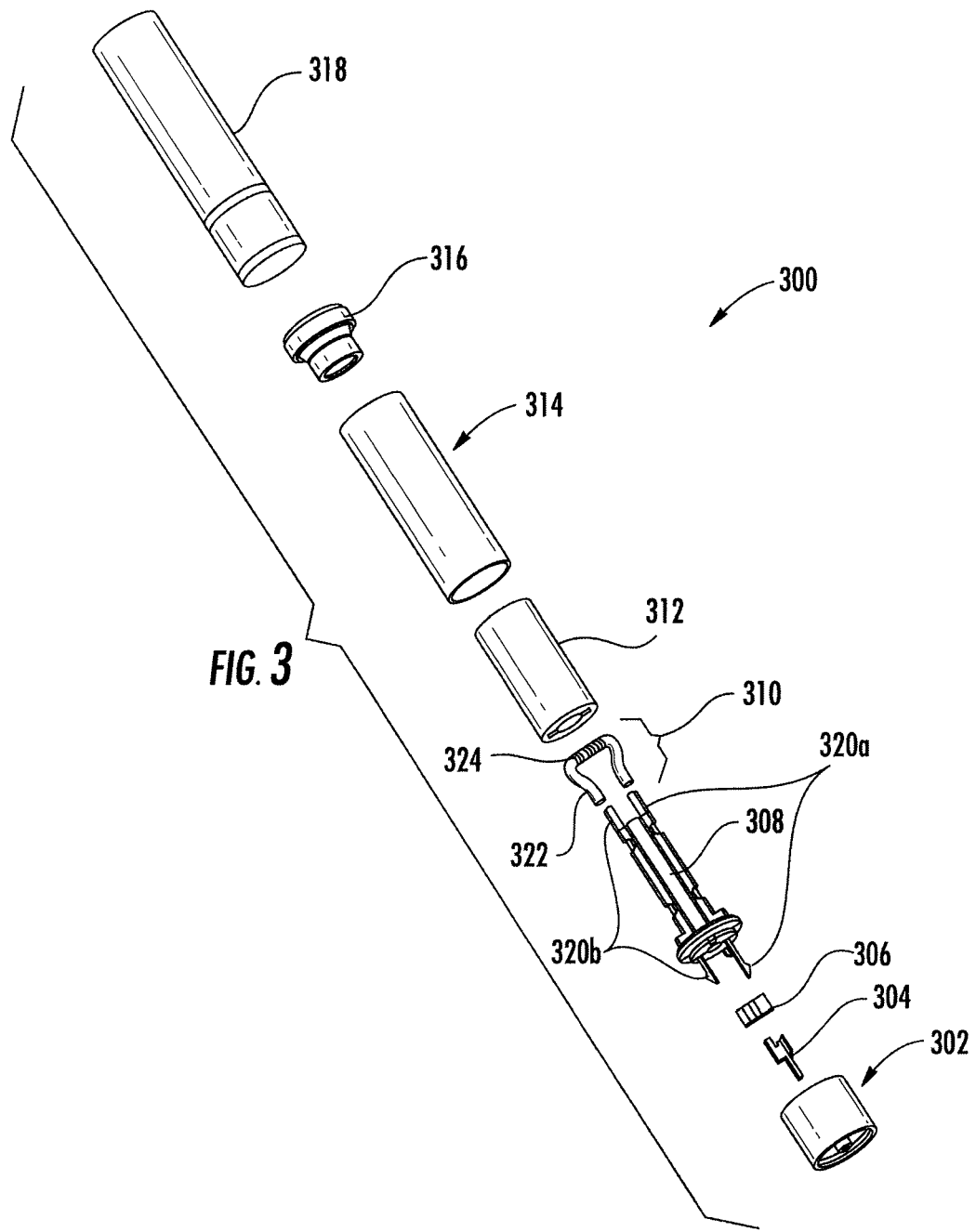

FIG. 3 illustrates the cartridge 300 in an exploded configuration. As illustrated, the cartridge 300 may comprise a base 302, a control component terminal 304, an electronic control component 306, a flow director 308, an atomizer 310, a reservoir substrate 312, an outer body 314, a mouthpiece 316, a label 318, and first and second heating terminals 320a, 320b according to an example embodiment of the present disclosure. The atomizer 310 may comprise a liquid transport element 322 and a heating element 324. The cartridge may additionally include a base shipping plug engaged with the base and/or a mouthpiece shipping plug engaged with the mouthpiece in order to protect the base and the mouthpiece and prevent entry of contaminants therein prior to use as disclosed, for example, in U.S. patent application Ser. No. 13/841,233 to Depiano et al., filed Mar. 15, 2013. The description included hereinafter provides example configurations of the above-described components and methods of assembly thereof. However, it should be understood that the cartridge 300 may be assembled in a variety of manners and may include additional or fewer components in other embodiments. For example, although the cartridge 300 is generally described herein as including a reservoir substrate, in other embodiments the cartridge may hold an aerosol precursor composition therein without the use of a reservoir substrate (e.g., through use of a container or vessel that stores the aerosol precursor composition or direct storage therein). In some embodiments, an aerosol precursor composition may be within a container or vessel that may also include a porous (e.g., fibrous) material therein.

Figure 4:
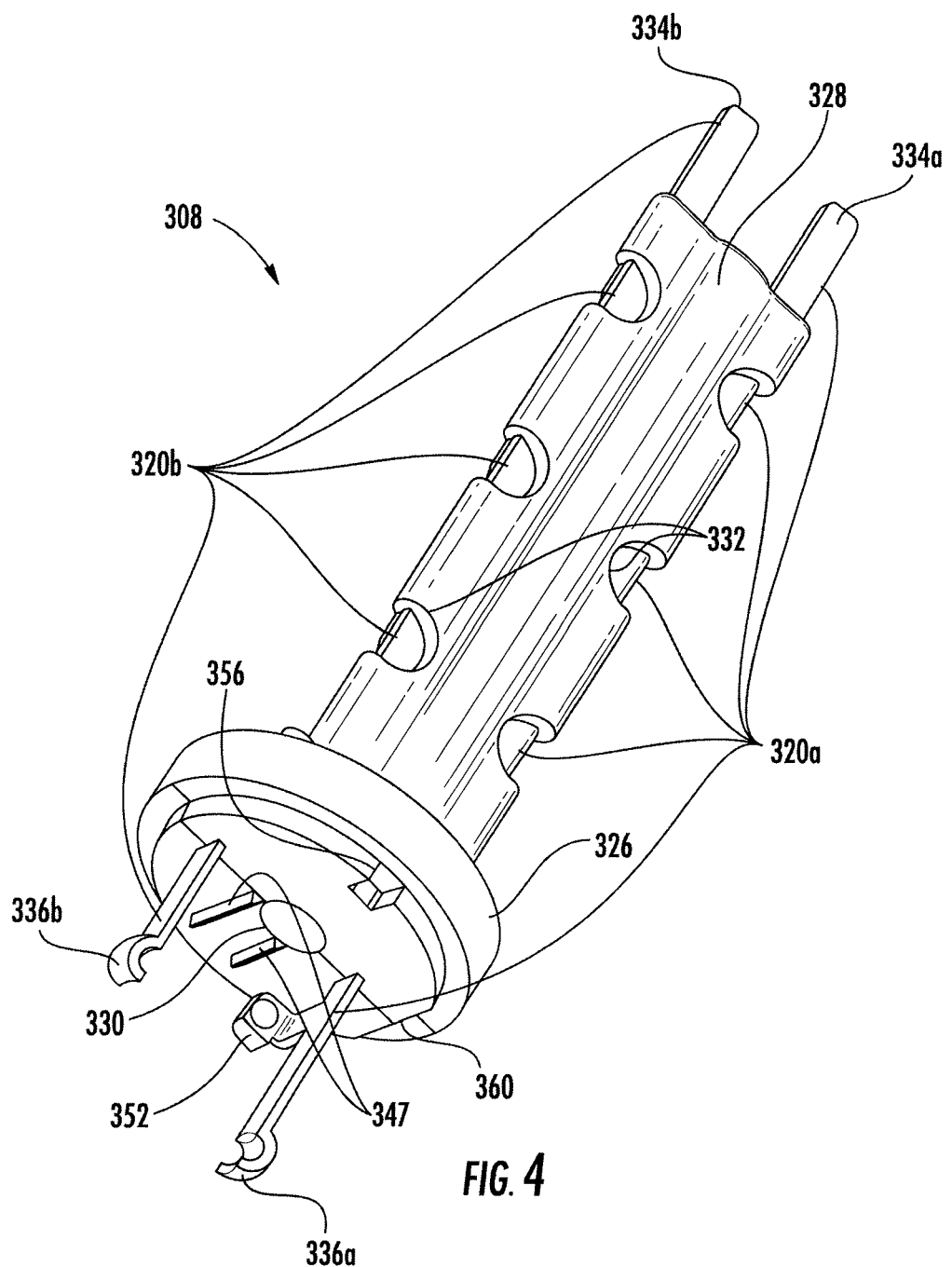
Figure 5:
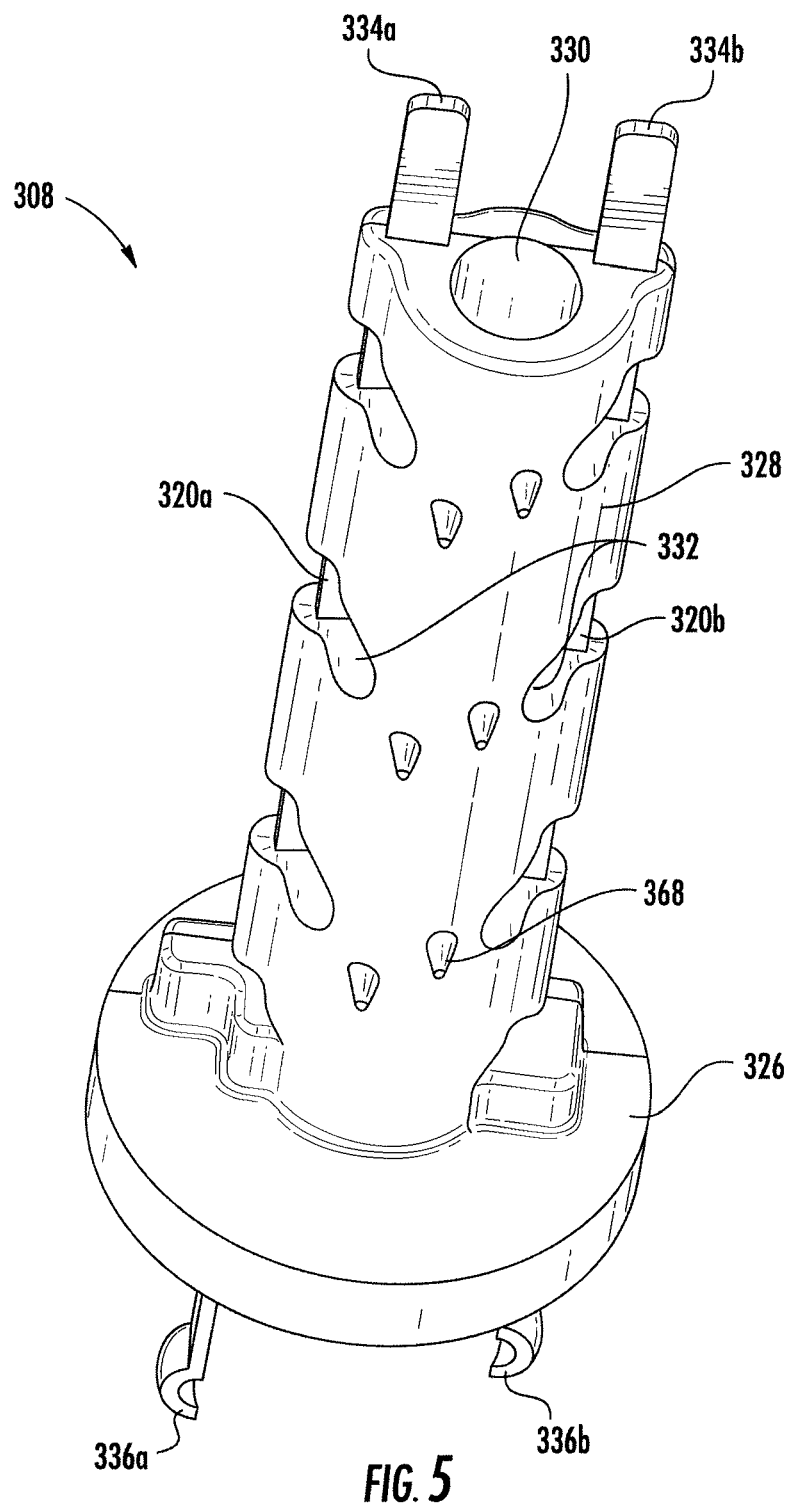

FIG. 4 illustrates a bottom perspective view of a back of the flow director 308 and the first and second heating terminals 320a, 320b, whereas FIG. 5 illustrates an opposing top perspective view of a front of the flow director and the heating terminals. As discussed hereinafter, the flow director 308 may be configured to direct a flow of air, which may be received from the control body 200, to the heating element 324 of the atomizer 310 (which is further described in relation to FIG. 9). Further, the first heating terminal 320a and the second heating terminal 320b (e.g., positive and ground terminals) are configured to engage opposing ends of the heating element 324 and form an electrical connection with the control body 200 when the cartridge 300 is connected thereto.

As illustrated in FIGS. 4 and 5, one or both of the heating terminals 320a, 320b may be coupled to the flow director 308. In the illustrated embodiment the first and second heating terminals 320a, 320b extend through the flow director 308. For example, one or both of the first and second heating terminals 320a, 320b may be molded into the flow director 308. By way of further example, the heating terminals 320a, 320b may be insert molded into the flow director 308. In this regard, in some embodiments the flow director 308 may comprise plastic or other material which may be shaped into a desired structure via a molding process.

Molding the heating terminals 320a, 320b into the flow director 308 may provide certain benefits. In this regard, molding the heating terminals 320a, 320b into the flow director 308 may allow for precise and secure placement of the heating terminals 320a, 320b with respect to one another and with respect to the flow director. Thereby, for example, a precise separation distance between the heating element terminals 320a, 320b may be set during the molding process and this separation distance may be maintained following the molding process by the resulting structure defined by the flow director 308. Additionally, providing the heating terminals 320a, 320b in secure engagement with the flow director 308 may further facilitate manufacturing of the cartridge 300 by providing a relatively large structure which may be more easily grasped and manipulated during manufacture of the cartridge. In this regard, the cartridge 300 of the present disclosure may be formed using automated manufacturing techniques as disclosed, for example, in U.S. patent application Ser. No. 14/227,159 to Ampolini et al., filed Mar. 27, 2014, which is incorporated herein by reference in its entirety.

Further, molding the heating terminals 320a, 320b into the flow director 308 may provide a seal between the heating terminals and the flow director. Thereby, fluid leakage between the heating terminals 320a, 320b and the flow director 308 may be substantially avoided. Thus, for example, leakage of aerosol precursor composition along the heating terminals 320a, 320b, which may otherwise occur during filing of the cartridge, may be substantially prevented. However, as may be understood, the heating terminals 320a, 320b may be sealed to the flow director 308 in other manners in embodiments in which the heating terminals are not molded into the flow director. For example, a sealant may be applied between the heating terminals 320a, 320b and the flow director 308 in embodiments in which the heating terminals extend through the flow director but are not molded therein.

In the illustrated embodiment the flow director 308 includes a base portion 326 and a longitudinal extension 328 extending therefrom. A through hole 330 may extend along the longitudinal length of the flow director 308 through the base portion 326 and the longitudinal extension 328. In this regard, the longitudinal extension 328 may define a tube surrounding the through hole 330. The through hole 330 may be configured to direct a flow of air, which may be received through the base 302 from the control body 200 or the coupler 202, through the base portion 326 and the longitudinal extension 328 to the heating element 324 of the atomizer 310. In this regard, in some embodiments the coupler 202 of the control body 200 (see, e.g., FIG. 3) may define an inlet through which ambient air enters and travels to the base 302 of the cartridge as described, for example, in U.S. patent application Ser. No. 13/840,264, filed Mar. 15, 2013, and U.S. application Ser. No. 14/193,961 to Worm et al., filed Feb. 28, 2014, which are incorporated herein by reference in their entireties. However, air may enter the cartridge in a variety of differing manners in other embodiments.

As illustrated, in some embodiments the heating elements may extend through the base portion 326 and the longitudinal extension 328. The longitudinal extension 328 may include cutouts 332 defined therein at which the heating terminals 320a, 320b may be exposed. The cutouts 332 may allow for formation of the flow director 308 with less material and/or allow for grasping the heating terminals 320a, 320b during the molding process so as to allow for precise placement of the heating terminals within the flow director as described above.

The heating terminals 320a, 320b may extend out of the flow director 308 at opposing ends thereof. In this regard, the first heating terminal 320a may extend out of the longitudinal extension 328 to define a first tab 334a and the second heating terminal 320b may extend out of the longitudinal extension to define a second tab 334b. Accordingly, the heating element 324 (see, e.g., FIG. 3) may be coupled (e.g., welded) to the heating terminals 320a, 320b such that current may be directed therethrough.

At an opposing end of the flow director 308, the first heating terminal 320a may extend out of the base portion 326 to define a first end 336a and the second heating terminal 320b may extend out of the base portion 326 to define a second end 336b. The ends 336a, 336b of the heating terminals 320a, 320b may be configured to engage electrical contacts in the coupler 202 of the control body 200 (see, e.g., FIG. 2). In some embodiments the electrical contacts in the coupler 202 may comprise circular metal bands of varying radii positioned at differing depths within the coupler as described in U.S. patent application Ser. No. 13/841,233 to DePiano et al., filed Mar. 15, 2013, which is incorporated herein by reference in its entirety.

Figure 6:
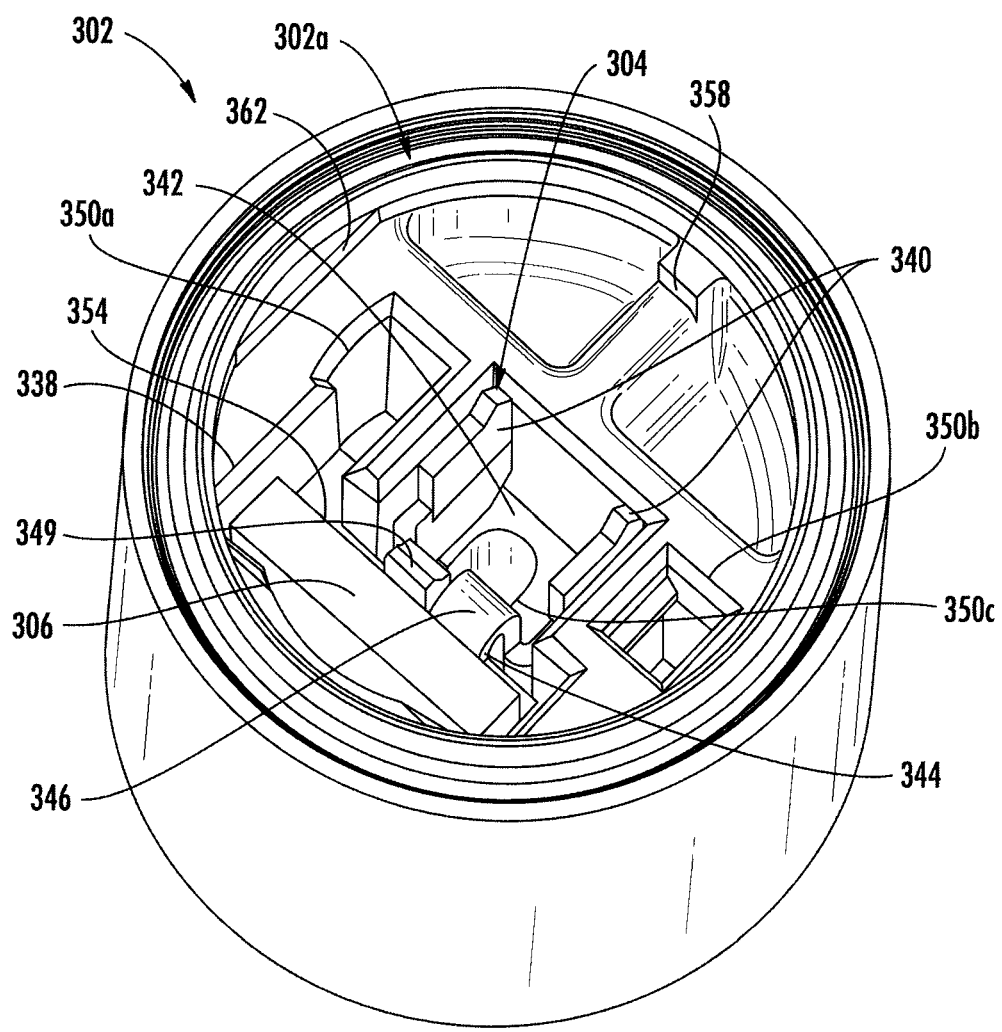

FIG. 6 illustrates an enlarged perspective view of the base 302. As illustrated, the base 302 may define a recess 338 configured to receive the electronic control component 306 therein. Additionally, the control component terminal 304 may be engaged with the base 302. As illustrated, the control component terminal 304 may include one or more wings 340. The wings 340 may be configured to engage a ledge 342 defined in the base 302 and/or walls extending perpendicularly thereto so as to securely hold the control component terminal 304 in the base and substantially prevent movement thereof.

A first end 344 of the control component terminal 304 may be configured to engage the electronic control component 306. The control component terminal 304 may define a reverse bend 346 configured to engage a contact 348 (see, e.g., FIG. 11) on the electronic control component 306. In this regard, the first end 344 of the control component terminal 304 may extend downwardly and into the recess 338 such that the electronic control component 306 may be inserted following coupling of the control component terminal to the base 302 to provide a secure connection therebetween. For example, the reverse bend 346 may cause the control component terminal 304 to act as a spring that biases the first end 344 thereof into contact with the electronic control component 306. However, in other embodiments the electronic control component 306 may be inserted into the base 302 before the control component terminal 304.

Figure 7:
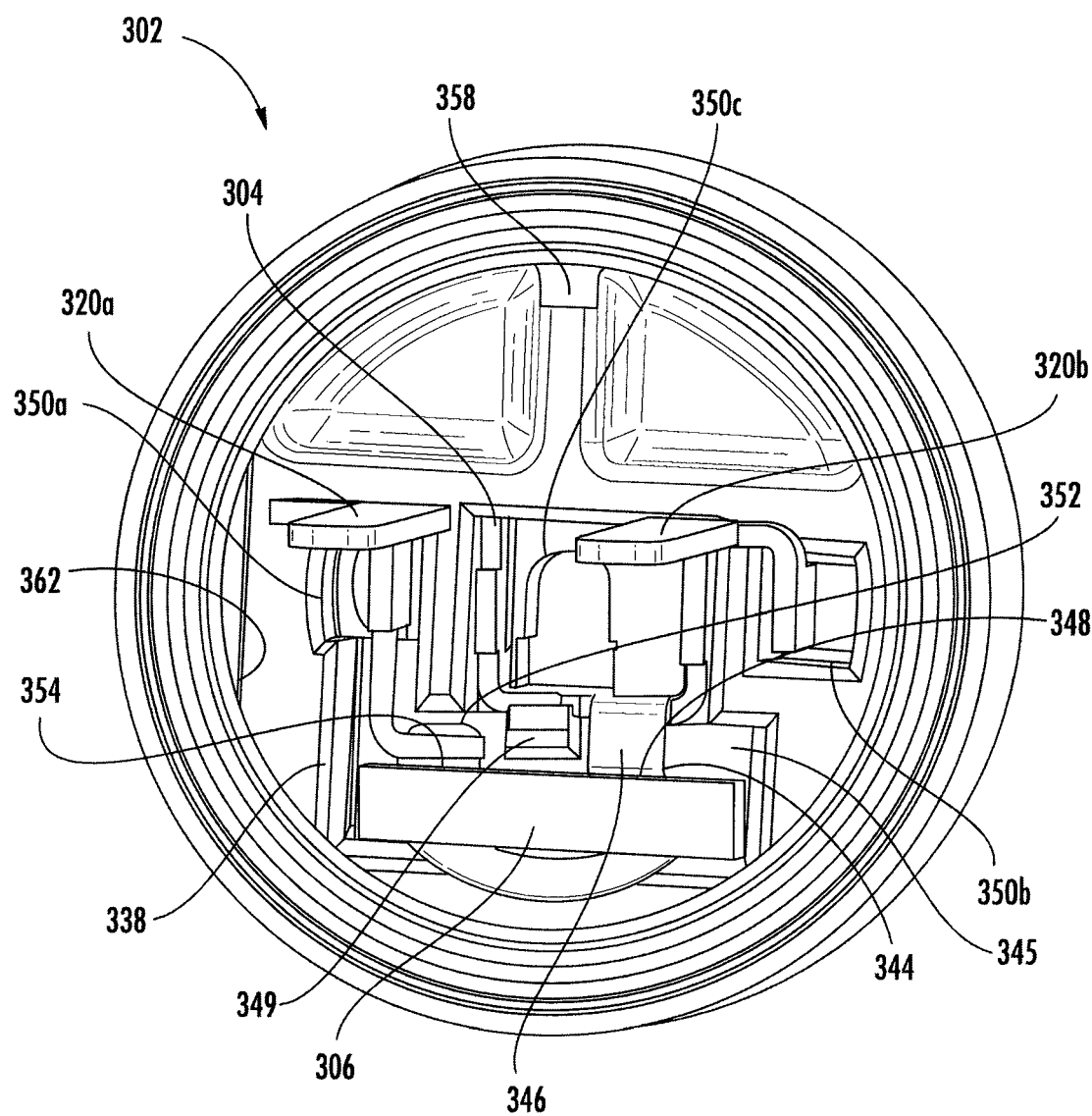

FIG. 7 illustrates a top perspective view of the base 302 following insertion of the heating terminals 320a, 320b, wherein the flow director 308 is not shown for clarity purposes. As illustrated therein, the base 302 may additionally include a ledge 345 configured to support the electronic control component 306 thereon. In this regard, the flow director 308 may include one or more deformable ribs 347 (see, FIG. 4) configured to engage the electronic control component 306 when the flow director is coupled to the base 302. Accordingly, the deformable ribs 347 may engage the electronic control component 306 such that the electronic control component is tightly sandwiched between the deformable ribs 347 and the ledge 345 in the base 302. Thus, the electronic control component 306 may be securely locked in place such that vibration may not cause the electronic control component to become loose or disconnect from the terminals in contact therewith.

Additionally, features may be provided that are configured to retain the control component terminal 304 in a desired position with respect to the electronic control component 306. In this regard, as illustrated in FIGS. 6 and 7, the base may define a clip 349. The clip 349 may be configured to define an interference fit relationship with respect to the control component terminal 304 such that the control component terminal is sandwiched between the clip 349 and the ledge 342. Thus, the control component terminal 304 may be securely locked in place such that vibration may not cause the control component 306 to become loose or disconnect from the electronic control component 306.

As further illustrated in FIG. 7, the base 302 may define a plurality of apertures 350a-c extending therethrough. A first aperture 350a may be configured to receive the first heating terminal 320a, a second aperture 350b may be configured to receive the second heater terminal 350b, and a third aperture 350c may be configured to receive the control component terminal 304. Accordingly, the control component terminal 304 may be inserted into the third aperture 350c, the first heating terminal 320a may be inserted into the first aperture 350a, and the second heating terminal 320b may be inserted into the second aperture 350b, as illustrated in FIG. 7.

As the first heating terminal 320a and the second heating terminal 320b are respectively inserted into the first and second apertures 350a, 350b, the base 302 may slightly bend the heating terminals away from a central axis extending through the cartridge 300. In this regard, the base 302 may define first and second protrusions 351a, 351b (see, FIG. 14)

respectively configured to bend the first and second heating terminals 320a, 320b outwardly. By bending the first and second heating terminals 320a, 320b in this manner, the ends 336a, 336b (see, e.g., FIG. 4) of the heating terminals may be positioned and configured with a spring bias to securely engage electrical contacts in the coupler 202 of the control body 200 (see, e.g., FIG. 2) and provided with a clearance for movement during engagement with the electrical contacts. Note that the particular direction in which the heating terminals are bent may vary depending on the configuration of the electrical contacts within the control body.

The first heating terminal 320a may define a ground protrusion 352. The ground protrusion 352 may be configured to contact a ground terminal 354 on the electronic control component 306 so as to provide ground thereto. Accordingly, the ground protrusion 352 may engage the ground terminal 354 during insertion of the first heating terminal 320a into the first aperture 350a in the base 302.

As noted above, the heating terminals 320a, 320b may be coupled to the flow director 308. Thus, the flow director 308 may be engaged with the base 302 substantially simultaneously with inserting the heating terminals 320a, 320b through the first and second apertures 350a, 350b in the base to define the configuration illustrated in FIG. 8. It may be important to provide a particular rotational alignment of the base 302 with respect to the flow director 308 about a longitudinal axis extending therethough. For example, a proper rotational alignment between the base 302 and the flow director 308 may ensure alignment of the heating terminals 320a, 320b in the first and second apertures 350a, 350b and proper alignment of the ground protrusion 352 with respect to the ground terminal 354. Accordingly, the base 302 and/or the flow director 308 may include features configured to ensure proper rotational alignment therebetween.

In this regard, as illustrated in FIG. 4, a notch 356 may be defined in the flow director 308, for example in the base portion 326 thereof. Further an inwardly-extending protrusion 358 may be defined at the base 302, as illustrated in FIGS. 6 and 7. Accordingly, the inwardly-extending protrusion 358 may engage the notch 356 to prevent rotation of the base 302 with respect to the flow director 308 and provide for alignment thereof. Additionally, the flow director 308 may include a flat cutout 360 (see, e.g., FIG. 4) and the base 302 may include a corresponding flat extension 362 (see, e.g., FIGS. 6 and 7) configured to engage the flat cutout to prevent rotation of the base with respect to the flow director and provide for alignment thereof. However, as may be understood, the base 302 may be keyed to the flow director 308 in a variety of other manners to ensure rotational alignment thereof and prevent rotational movement therebetween.

Figure 8:
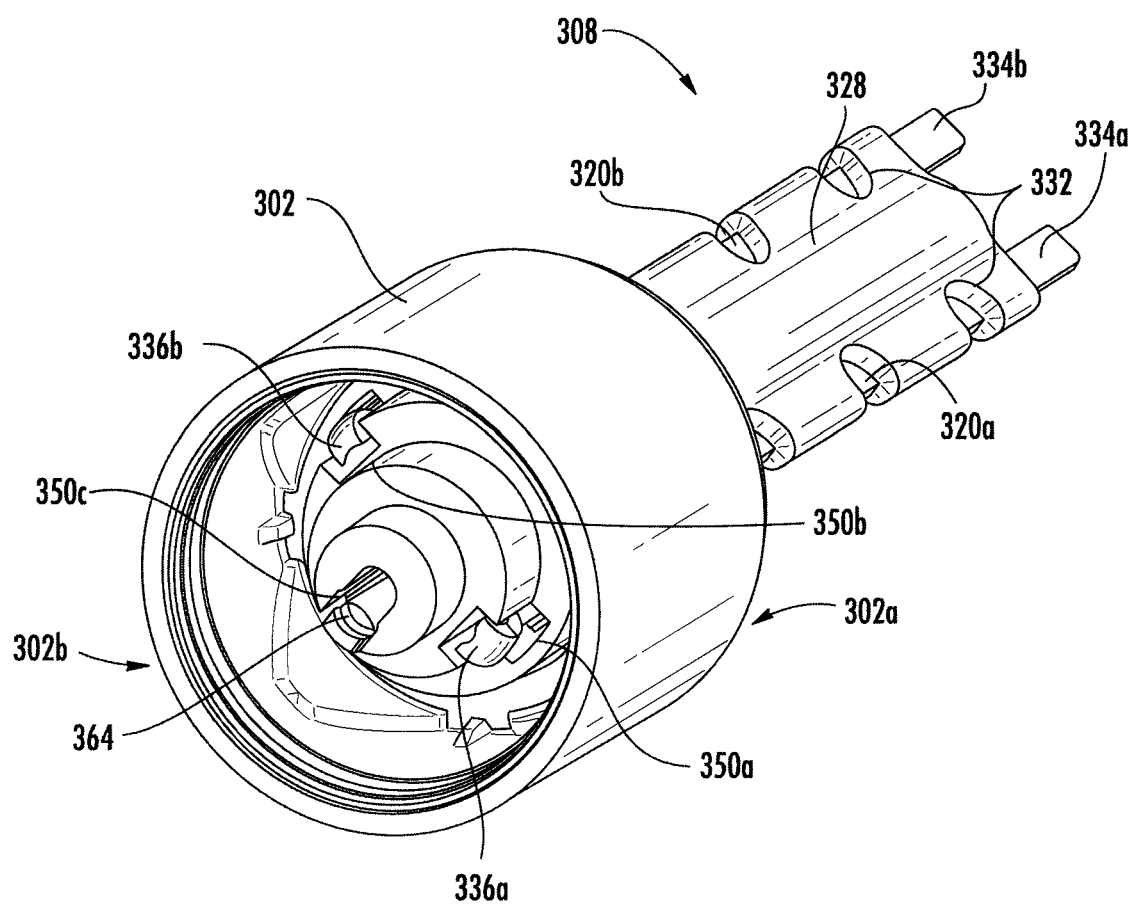

In this regard, FIG. 8 illustrates the flow director 308 coupled to an inner end 302a of the base 302. In some embodiments the base 302 may be sealed to the flow director 308. Various embodiments of mechanisms and manners may be employed to seal the base 302 to the flow director 308. For example, the base 302 may be welded to the flow director 308 or the base may be adhered to the flow director via a glue, adhesive, or sealant. With respect to welding, various embodiments of methods thereof may be employed depending on the particular materials from which the flow director 308 and the base 302 are formed. For example, arc welding, gas welding, resistance welding, energy beam welding, and solid-state welding may be employed. An example of a solid-state welding process is ultrasonic welding which uses ultrasonic vibrations to create a weld between two workpieces held together under pressure. Another example of a solid-state welding process is induction welding, which uses electromagnetic induction to heat workpieces. However, in embodiments in which the base 302 and the flow director 308 are formed from plastic or other non-ferromagnetic materials, the material may be implanting with metallic or ferromagnetic compounds, called susceptors in order to allow for induction welding thereof. As may be understood, these welding methods may provide a hermetic seal. However, as noted above, various other embodiments of coupling and sealing mechanisms and methods may be employed.

As described above, the heating terminals 320a, 320b and the control component terminal 304 may extend through respective apertures 350a-c in the base 302. Thus, as illustrated in FIG. 8, the ends 336a, 336b of the heating terminals 320a, 320b may be exposed at a connector end 302b of the base 302 in order to engage electrical contacts in the coupler 202 of the control body 200. Further, the control component terminal 304 may extend from the electronic control component 306 through the third aperture 350c to a second end 364 positioned proximate the connector end 302b of the base 302.

Thus, when the control body 200 is coupled to the cartridge 300, the electronic control component 306 may form an electrical connection with the control body through the control component terminal 304. For example, the second end 364 of the control component terminal 304 may engage an electrical contact in the coupler 202 of the control body 200 (see, e.g., FIG. 2). The control body 200 may thus employ the electronic control component 306 to determine whether the cartridge 300 is genuine and/or perform other functions. Various examples of electronic control components and functions performed thereby are described in U.S. patent application Ser. No. 13/647,000, filed Oct. 8, 2012, which is incorporated herein by reference in its entirety. Further, in some embodiments the base 302 may comprise anti-rotation features that substantially prevent relative rotation between the cartridge 300 and the control body 200 when coupled together as disclosed in U.S. patent application Ser. No. 13/840,264, filed Mar. 15, 2013, which is incorporated herein by reference in its entirety.

Figure 9:
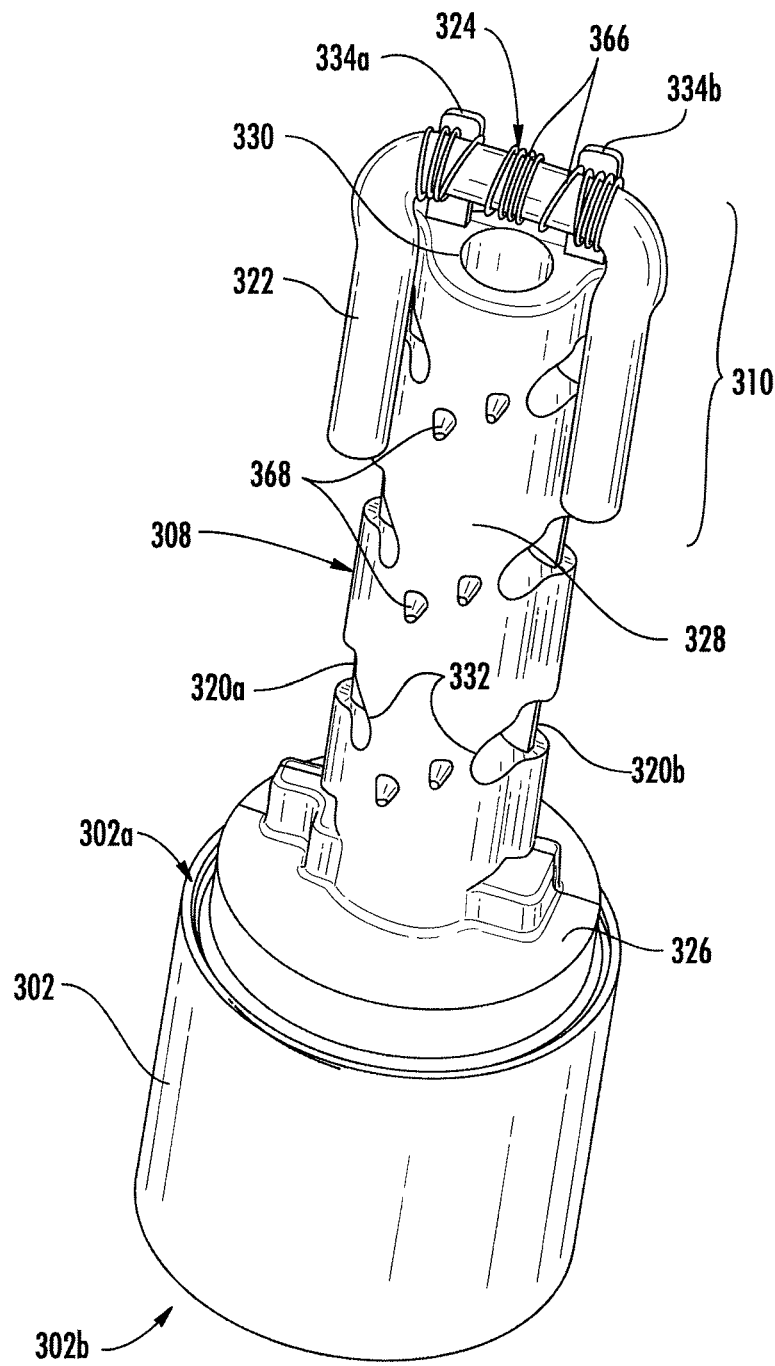

As illustrated in FIG. 9, the atomizer 310 may couple to the heating terminals 320a, 320b. For example, the atomizer 310 may be coupled to the heating terminals 320a, 320b after the base 302 is coupled to the flow director 308. Alternatively, the atomizer 310 may be coupled to the heating terminals 320a, 320b prior to coupling the flow director 308 to the base 302. In this regard, by coupling the heating terminals 320a, 320b to the flow director 308, the heating terminals may be securely retained at a desired separation distance, which may allow for coupling of the atomizer 310 thereto at any point in time.

As noted above, in one embodiment the atomizer 310 may include the liquid transport element 322 and the heating element 324. The heating element 324 may be in direct contact with the liquid transport element 322 so as to directly apply heat thereto. Various embodiments of materials configured to produce heat when electrical current is applied therethrough may be employed to form the heating element 324. Example materials from which the heating element 324 may be formed include Kanthal (FeCrAl), Nichrome, Molybdenum disilicide ($MoSi_2$), molybdenum silicide (MoSi), Molybdenum disilicide doped with Aluminum (Mo$(Si,Al)_2$), graphite and graphite-based materials; and ceramic (e.g., a positive or negative temperature coefficient ceramic). Accordingly, regardless of the particular configuration of the heating element 324 and the material thereof, current supplied from the control body 200 through the heating terminals 320a, 320b may be employed to produce heat at the heating element.

As illustrated in FIG. 9, in one embodiment the heating element 324 may comprise a wire defining a plurality of coils 366 wound about the liquid transport element 322. In some embodiments the heating element 324 may be formed by winding the wire about the liquid transport element 322 as described in U.S. patent application Ser. No. 13/708,381 to Ward et al., filed Dec. 7, 2012, which is incorporated herein by reference in its entirety. Further, in some embodiments the wire may define a variable coil spacing configured to provide a heating portion and contact portions for attachment to heating terminals, as described in U.S. patent application Ser. No. 13/827,994 to DePiano et al., filed Mar. 14, 2013, which is incorporated herein by reference in its entirety. Additionally, in some embodiments the heating portion of the heating element may define a variable coil spacing, as described in U.S. patent application Ser. No. 14/194,233 to DePiano et al., filed Feb. 28, 2014, which is incorporated herein by reference in its entirety.

However, various other embodiments of methods may be employed to form the heating element 324, and various other embodiments of heating elements may be employed in the atomizer 310. For example, a stamped heating element may be employed in the atomizer, as described in U.S. patent application Ser. No. 13/842,125 to DePiano et al., filed Mar. 15, 2013, which is incorporated herein by reference in its entirety. Various additional examples of heaters and materials employed to form heaters are described in U.S. Pat. App. Pub. No. 2014/0060554 to Collett et al., which is incorporated herein by reference, as noted above. Additionally, in various embodiments, one or more microheaters or like solid state heaters may be used. Example embodiments of microheaters and atomizers incorporating microheaters suitable for use in the presently disclosed devices are described in U.S. patent application Ser. No. 13/602,871, filed Sep. 4, 2012, which is incorporated herein by reference in its entirety.

The heating element 324 may be coupled to the tabs 334a, 334b of the heating terminals 320a, 320b via a variety of methods. For example, the heating element 324 may be crimped to the tabs 334a, 334b of the heating terminals 320a, 320b. Alternatively, the heating element 324 may be soldered to the tabs 334a, 334b of the heating terminals 320a, 320b. In an additional embodiment the heating element 324 may be coupled to the tabs 334a, 334b of the heating terminals 320a, 320b via clips or other mechanical fasteners. In another example embodiment the heating element 324 may be welded (e.g., laser or resistance welded) to the tabs 334a, 334b of the heating terminals 320a, 320b, as described, for example, in U.S. patent application Ser. No. 14/227,159 to Ampolini et al., filed Mar. 27, 2014, which is incorporated herein by reference in its entirety. However, as may be understood, the atomizer may be coupled to various other portions of the heating terminals and/or various other connection mechanisms (e.g., wires) and methods may be employed in other embodiments.

Figure 10:
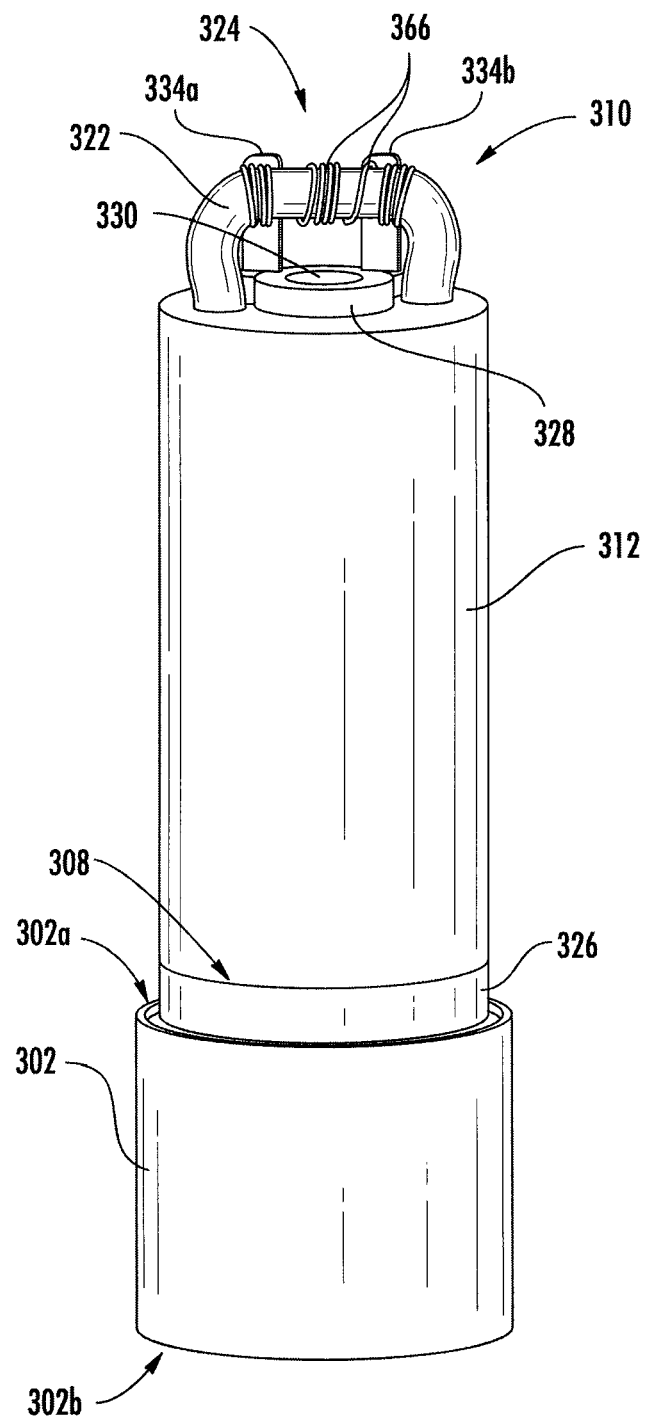

After coupling of the atomizer 310 to the heating terminals 320a, 320b, the reservoir substrate 312 may be positioned in contact with the liquid transport element 322 of the atomizer, as illustrated in FIG. 10. For example, the reservoir substrate 312 may be wrapped at least partially about the liquid transport element 322. Alternatively to wrapping the reservoir substrate around the liquid transport element, in another embodiment the liquid transport element may be positioned outside of, but still in contact with, the reservoir substrate. For example, the reservoir substrate may be wrapped around the flow director and the liquid transport element may be folded against the outer surface of the reservoir substrate.

The reservoir substrate 312 may comprise one or more layers of nonwoven fibers at least partially wrapped about the flow director 308. Thereby, for example, the reservoir substrate 312 may be substantially formed into the shape of a tube. In some embodiments first and second ends 312a, 312b of the reservoir substrate 312 may be out of contact with one another such that a gap 367 is defined between the first and second ends thereof (see, FIG. 13). However, in other embodiments the ends of the reservoir substrate 312 may overlap one another. Exemplary reservoir substrates formed of cellulose acetate fibers are described in U.S. patent application Ser. No. 13/802,950 to Chapman et al., filed Mar. 14, 2013, which is incorporated herein by reference in its entirety.

The aerosol precursor composition can be, for example, sorptively retained by the reservoir substrate 312. The reservoir substrate 312 is in fluid connection with the liquid transport element 322 due to the contact therebetween. Thus, the liquid transport element 322 may be configured to transport liquid from the reservoir substrate 312 to the heating element 324 via capillary action or other liquid transport mechanisms. In this regard, so long as physical contact between the reservoir substrate 312 and the liquid transport element 322 is provided, the aerosol precursor component may be transferred therebetween due to wicking characteristics of the liquid transport element. Thus, the liquid transport element 322 need not be configured to extend along an entirety of a longitudinal length of the reservoir substrate 312 in some embodiments.

As illustrated, the reservoir substrate 312 may also be wrapped and extend at least partially around the flow director 308 in addition to the liquid transport element 322. The flow director 308 may include particular features configured to facilitate wrapping of the reservoir substrate 312 thereabout and retention of the reservoir substrate in a selected position thereon. In this regard, as illustrated in FIG. 9, the flow director 308 may include one or more protrusions 368 extending therefrom. As illustrated, in one embodiment the protrusions 368 may define a substantially conical configuration (e.g., a truncated conical configuration) in some embodiments. Thereby, the protrusions 368 may extend into the material defining the reservoir substrate 312 to provide for engagement therebetween. However, protrusions defining various other shapes configured to engage the reservoir substrate (e.g., a hook configuration) may be employed in other embodiments.

By providing engagement between the flow director 308 and the reservoir substrate 312, the reservoir substrate may be securely coupled to the flow director, which may help to retain the reservoir substrate in a desired position. In this regard, the reservoir substrate 312 may otherwise be prone to movement during insertion of the flow director 308 and the reservoir substrate into the outer body 314. In some embodiments the outer body 314 may be inserted over the reservoir substrate using a funnel-shaped tool as described, for example, in U.S. patent application Ser. No. 14/227,159 to Ampolini et al., filed Mar. 27, 2014, which is incorporated herein by reference in its entirety.

Figure 11:
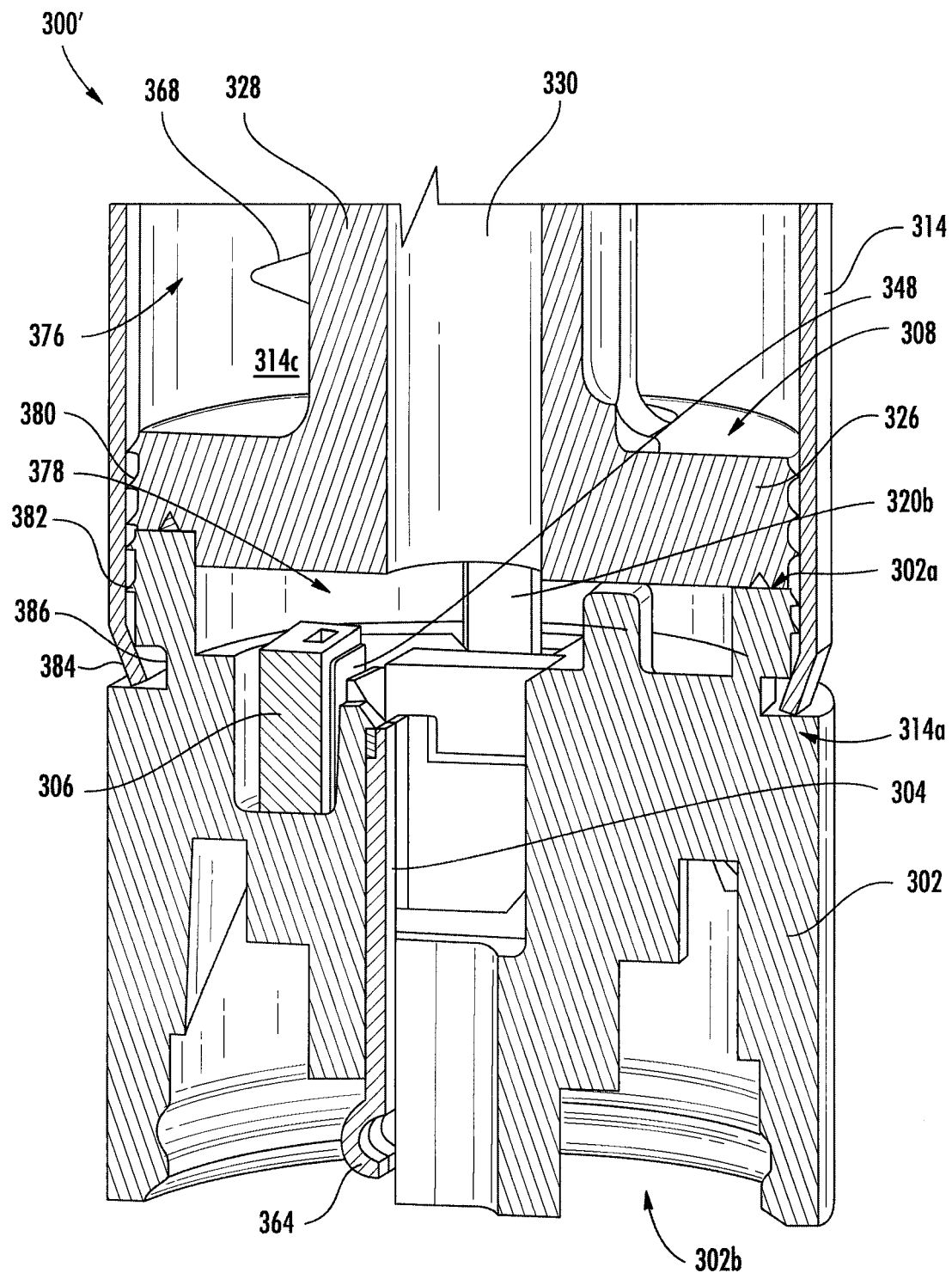

FIG. 11 illustrates a partial sectional view through a first embodiment of the cartridge 300' along line 11-11 from FIG. 2, wherein the reservoir substrate (see, e.g., FIG. 3) is hidden for clarity purposes, following coupling of the outer body 314 thereto. As illustrated, in some embodiments the outer body 314 may be directly coupled to the base 302. As further illustrated in FIG. 11, in some embodiments the outer body 314 may be directly coupled to the flow director 308. In other words, the outer body 314 may directly contact the base 302 and the flow director 308.

The flow director 308 and the outer body 314 may define a first compartment 376. In particular, the flow director 308 may contact the outer body 314 such that the flow director and the outer body collectively define and at least partially surround the first compartment 376. In some embodiments the first compartment 376 may be configured to receive the reservoir substrate 312. Accordingly, the first compartment 316 may also be referred to as a reservoir compartment 376. As illustrated, in some embodiments the reservoir compartment 376 may define a substantially annular configuration as a result of the reservoir compartment extending between the outer body 314, which may define a tubular configuration, and the flow director 308, which may extend along at least a portion of a length of the outer body proximate a center thereof.

The flow director 308 and the base 302 may define a second compartment 378. In particular, the flow director 308 may contact (e.g., directly contact) the base 302 such that the flow director and the base collectively define and at least partially surround the second compartment 378. The second compartment 378 may also be referred to as an electronics compartment 378 in embodiments in which one or more electronic components are at least partially received therein. For example, in the embodiment illustrated in FIG. 11, the control component terminal 304 and the electronic control component 306 are received therein.

The first compartment 376 and the second compartment 378 are referred to hereinafter as the reservoir compartment 376 and the electronics compartment 378. However, reference to the compartments 376, 378 in this manner is provided for purposes of simplicity. In this regard, as noted above, in some embodiments the first compartment 376 may not include the reservoir substrate 312 and/or the second compartment 378 may not include electronic components such as the control component terminal 304 and the electronic control component 306.

The flow director 308 may be coupled to the outer body 314 via a variety of manners and via a variety of mechanisms. Similarly the flow director 308 may be coupled to the base 302 in a variety of manners and via a variety of mechanisms. The mechanisms and manners of coupling employed may depend on the particular structural relationship of the flow director 308, the outer body 314, and the base 302 as well as the material compositions thereof.

In some embodiments the base 302, the flow director 308, and/or the outer body 314 may be configured to avoid leakage of fluid. In this regard, for example, leakage of the aerosol precursor composition out of the reservoir compartment 376 to an exterior environment may be undesirable. For example, such leakage may decrease the useable life of the cartridge by decreasing the amount of aerosol precursor composition available for vaporization. Additionally, leakage of the aerosol precursor composition from the reservoir compartment 376 into the electronics compartment 378 may be undesirable. In this regard, the aerosol precursor composition could damage the electronic control component 306 and/or leak along the control component terminal 304 to the control body 200 (see, e.g., FIG. 2), which could also be damaged.

Accordingly, in order to avoid any such fluid leakage, the flow director 308 may seal against the outer body 314. For example, in the embodiment illustrated in FIG. 11, the base portion 326 of the flow director 308 seals against an inner surface 314c of the outer body 314. As illustrated, in one embodiment the base portion 326 of the flow director 308 may define at least one deformable rib 380 configured to seal against an inner surface 314c of the outer body 314. In this regard, each of the deformable ribs 380 may extend continuously around the perimeter of the base portion 326 of the outer body 308 and initially extend to an outer dimension (e.g., an outer diameter in embodiments in which the outer body is tubular) equal to, or slightly greater than an inner dimension (e.g., a diameter) of the outer body 314 at the inner surface 314c.

Thereby, the deformable ribs 380 may deform upon coupling of the outer body 314 to the flow director 308 to define a tight seal with the inner surface 314c of the outer body. For example, the outer body 314 may comprise a metal such as stainless steel and the flow director 308 may define a relatively softer material such as plastic that is configured to deform during insertion into the outer body. By sealing the flow director 308 against the inner surface 314c of the outer body 314, leakage from the reservoir compartment 376 between the outer body and the flow director may be avoided.

In the illustrated embodiment the flow director 308 includes three deformable ribs 380. However, in other embodiments the flow director 308 may include a plurality of deformable ribs 380 and particularly may include from one deformable rib to six deformable ribs. Use of multiple deformable ribs 380 at the flow director 308 may be desirable in that the additional deformable ribs may provide redundant protection in the event that the aerosol precursor composition leaks past a first deformable rib. However, as noted above, the flow director 308 may include a single deformable rib 380 in other embodiments.

Accordingly, the deformable ribs 380 at the base portion 326 of the flow director 308 may resist leakage of the aerosol precursor composition between the outer body 314 and the flow director. Further, as noted above, in some embodiments the base 302 may be sealed to the flow director 308 (e.g., welded thereto). Accordingly, in the event that the aerosol precursor leaks past the deformable ribs 380 at the base portion 326 of the flow director 308, the seal between the flow director and the base 302 may prevent entry of the aerosol precursor composition into the electronics compartment 378.

As further illustrated in FIG. 11, the outer body 314 may couple to the base 302. For example, the base 302 may be directly coupled to a first end 314a of the outer body 314. In this regard, the base 302 may define at least one deformable rib 382 configured to seal against the inner surface 314c of the outer body 314. By sealing the base 302 against the inner surface 314c of the outer body 314, the base may further resist leakage of the aerosol precursor composition from the reservoir compartment 376. In this regard, each deformable ribs 382 may extend continuously around the perimeter of the inner end 302a of the base 302 and initially extend to an outer dimension (e.g., an outer diameter in embodiments in which the outer body is tubular) equal to, or slightly greater than an inner dimension (e.g., a diameter) of the outer body 314 at the inner surface 314c.

Thereby, the deformable ribs 382 may deform upon coupling of the outer body 314 to the base 302 to define a tight seal with the inner surface 314c of the outer body. For example, the outer body 314 may comprise a metal such as stainless steel and the base 302 may define a relatively softer material such as plastic that is configured to deform during insertion of the inner end 302*a* into the outer body. By sealing the base 302 against the inner surface 314*c* of the outer body 314, leakage from the reservoir compartment 376 between the outer body and the base may be avoided.

In the illustrated embodiment the base 302 includes two deformable ribs 382. However, in other embodiments the base 302 may include a plurality of deformable ribs 382 and particularly may include from one deformable rib to six deformable ribs. Use of multiple deformable ribs 382 at the base 302 may be desirable in that the additional deformable ribs may provide redundant protection in the event that the aerosol precursor composition leaks past the base portion 326 of the flow director 308 and further leaks past a first deformable rib 382 of the base 302. However, as noted above, the base 302 may include a single deformable rib 382 in other embodiments.

As may be understood, deformable ribs may alternatively or additionally be placed at the inner surface 314*c* of the outer body 314 in order to contact the flow director 308 and/or the base 302. Accordingly, the deformable ribs 380 of the flow director 308 and the deformable ribs 382 of the base 302 and/or the outer body 314 may deform during the engagement therebetween such that a tight seal is formed between the outer body and the flow director and between the base and the flow director so as to resist fluid leakage as described above.

As further illustrated in FIG. 11, in some embodiments the outer body 314 may be crimped so as to provide a secure coupling between the outer body and the base 302 and/or the flow director 308. For example, in the illustrated embodiment the outer body 314 may be crimped proximate the first end 314*a* to define a crimp 384 extending into a groove 386 defined in and at least partially extending around the perimeter of the inner end 302*a* of the base 302. Thereby, engagement between the crimp 384 and the groove 386 may secure the outer body 314 to the base 302 and may further resist leakage by ensuring a tight seal against one or more of the deformable ribs 380, 382. In some embodiments, in order to facilitate crimping of the outer body 314, the outer body may comprise a metal that is relatively ductile, such as stainless steel. Use of stainless steel may also be beneficial in that it may resist corrosion. However, various other embodiments of materials that are relatively ductile may be employed.

By sealing the reservoir compartment 376 in one or more manners, fluid leakage from the reservoir compartment to the electronics compartment 378 may be avoided. In this regard, by positioning the control component terminal 306 in the electronics compartment 378, the control component terminal may not extend into the reservoir compartment 376. Thereby, leakage of aerosol precursor composition along the control component terminal 306, which may otherwise occur in instances in which the cartridge is overfilled or filled at a rate that exceeds a rate of absorption of the reservoir substrate 312, may be avoided. Further, sealing the reservoir compartment 376 may protect the electronic control component 304 from damage from the aerosol precursor composition.

Although embodiments of the present disclosure are directed to avoiding leaking of the aerosol precursor composition from the reservoir compartment 376 and/or entry of the aerosol precursor composition into the electronics compartment 378, the particular construction of the cartridge configured to provide these benefits may vary. In this regard, whereas the embodiment of the cartridge 300' described above and illustrated in FIG. 11 includes deformable ribs 380, 382 and the base 302 is directly coupled to the outer body 314, in other embodiments the construction of the cartridge may vary.

For example, FIG. 12 illustrates a partial sectional view through a second embodiment of the cartridge 300" along line 11-11 from FIG. 2. In the embodiment of the cartridge 300" illustrated in FIG. 12, the base 302 is indirectly coupled to the outer body 314 and other sealing configurations are employed. In this regard, in the embodiment of the cartridge 300" illustrated in FIG. 12, the flow director 308 is coupled to the outer body 314. Further, the base 302 is coupled to the flow director 308. More particularly, the outer body 314 and the base 302 are directly coupled to the base portion 326 of the flow director 308. Accordingly, the base 302 may be indirectly coupled to the outer body 314 via direct coupling with the flow director 308.

As illustrated, in one embodiment the base portion 326 of the flow director 308 may extend to define a shape and size corresponding to a size and shape of an outer surface 314*d* of the outer body 314 and/or an outer surface 302*d* of the base 302. For example, in the illustrated embodiment the base portion 326 of the flow director 308, the outer body 314, and the base 302 are each round and extend to substantially the same diameter. Thereby, the cartridge 300" may define an exterior that appears to be integral, despite the exterior being formed from the base 302, the flow director 308, and the outer body 314.

Further, in some embodiments a first recessed portion 388 of the base portion 326 of the flow director 308 may contact the inner surface 314*c* of the outer body 314. Alternatively or additionally, a second recessed portion 390 of the base portion 326 of the flow director 308 may contact an inner surface 302*c* of the base 302. Accordingly, by engaging the inner surface 314*c* of the outer body 314 and/or the inner surface 302*c* of the base 302 with the base portion 326 of the flow director 308, engagement between the flow director and the outer body and/or between the flow director and the base may be improved. In this regard, in addition to the sealing mechanisms and methods described above, interference fit may improve the connection between the flow director 308 and the outer body 314 and/or improve the connection between the flow director and the base 302.

The flow director 308 may be coupled to the base 302 via a variety of mechanisms and methods. In this regard, welding and various other methods for attaching the base 302 to the flow director 308 which may also be employed in the cartridge 300" are described above. As further noted above, in some embodiments the coupling between the base 302 and the flow director 308 may produce a seal therebetween to prevent ingress of fluids such as the aerosol precursor composition into the electronics compartment 378.

Similarly, the flow director 308 may be coupled to the outer body 314 via a variety of mechanisms and manners. In some embodiments the outer body 314 may be sealed to the flow director 308. For example, the outer body 314 may be welded to the flow director 308 or the outer body may be adhered to the flow director via a glue, adhesive, epoxy, or sealant. With respect to welding, various embodiments of methods thereof may be employed depending on the particular materials from which the flow director 308 and the outer body 314 are formed. For example, arc welding, gas welding, resistance welding, energy beam welding, and solid-state welding may be employed. An example of a solid-state welding process is ultrasonic welding which uses ultrasonic vibrations to create a weld between two workpieces held together under pressure. Another example of a solid-state welding process is induction welding, which uses electromagnetic induction to heat workpieces. However, in embodiments in which the outer body 314 and the flow director 308 are formed from plastic or other non-ferromagnetic materials, the material may be implanting with metallic or ferromagnetic compounds, called susceptors in order to allow for induction welding thereof. As may be understood, use of these welding methods may provide a hermetic seal which may retain the aerosol precursor composition in the reservoir compartment 376. However, various other embodiments of coupling mechanisms and methods may be employed.

As described above, the flow director 308 and the base may cooperatively define the electronics compartment 378. Further, the flow director 308 and the outer body 314 may cooperatively define the reservoir compartment 376. As part of the formation of the compartments 376, 378, certain sealing arrangements may be employed. For example, as described above, the flow director 308 may be sealed to the outer body 314 and the flow director may be sealed to the base 302. Accordingly, by sealing the reservoir compartment 376, the likelihood of egress of the aerosol precursor composition therefrom may be reduced. Further, by providing separate compartments for the reservoir substrate 312 and the electronic control component 306, wherein at least one seal is positioned therebetween, the likelihood of the aerosol precursor composition damaging the electronic control component 306 may be reduced.

As noted above, embodiments of the present disclosure are directed to avoiding leakage of fluid from the reservoir compartment 376. In particular, embodiments of the present disclosure are directed to avoiding leakage of an aerosol precursor composition from the reserve In this regard, following attachment of the outer body 314, the reservoir compartment 376 may be filled with the aerosol precursor composition.

The aerosol precursor, or vapor precursor composition, can vary. Most preferably, the aerosol precursor is composed of a combination or mixture of various ingredients or components. The selection of the particular aerosol precursor components, and the relative amounts of those components used, may be altered in order to control the overall chemical composition of the mainstream aerosol produced by the aerosol generating piece. Of particular interest are aerosol precursors that can be characterized as being generally liquid in nature. For example, representative generally liquid aerosol precursors may have the form of liquid solutions, viscous gels, mixtures of miscible components, or liquids incorporating suspended or dispersed components. Typical aerosol precursors are capable of being vaporized upon exposure to heat under those conditions that are experienced during use of the aerosol generating pieces that are characteristic of the current disclosure; and hence are capable of yielding vapors and aerosols that are capable of being inhaled.

For aerosol delivery systems that are characterized as electronic cigarettes, the aerosol precursor most preferably incorporates tobacco or components derived from tobacco. In one regard, the tobacco may be provided as parts or pieces of tobacco, such as finely ground, milled or powdered tobacco lamina. In another regard, the tobacco may be provided in the form of an extract, such as a spray dried extract that incorporates many of the water soluble components of tobacco. Alternatively, tobacco extracts may have the form of relatively high nicotine content extracts, which extracts also incorporate minor amounts of other extracted components derived from tobacco. In another regard, components derived from tobacco may be provided in a relatively pure form, such as certain flavoring agents that are derived from tobacco. In one regard, a component that is derived from tobacco, and that may be employed in a highly purified or essentially pure form, is nicotine (e.g., pharmaceutical grade nicotine).

The aerosol precursor may incorporate a so-called "aerosol forming materials." Such materials have the ability to yield visible aerosols when vaporized upon exposure to heat under those conditions experienced during normal use of aerosol generating pieces that are characteristic of the current disclosure. Such aerosol forming materials include various polyols or polyhydric alcohols (e.g., glycerin, propylene glycol, and mixtures thereof). Many embodiments of the present disclosure incorporate aerosol precursor components that can be characterized as water, moisture or aqueous liquid. During conditions of normal use of certain aerosol generating pieces, the water incorporated within those pieces can vaporize to yield a component of the generated aerosol. As such, for purposes of the current disclosure, water that is present within the aerosol precursor may be considered to be an aerosol forming material.

It is possible to employ a wide variety of optional flavoring agents or materials that alter the sensory character or nature of the drawn mainstream aerosol generated by the aerosol delivery system of the present disclosure. For example, such optional flavoring agents may be used within the aerosol precursor to alter the flavor, aroma and organoleptic properties of the aerosol. Certain flavoring agents may be provided from sources other than tobacco. Exemplary flavoring agents may be natural or artificial in nature, and may be employed as concentrates or flavor packages.

Exemplary flavoring agents include vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, cinnamon, sandalwood, jasmine, cascarilla, cocoa, licorice, and flavorings and flavor packages of the type and character traditionally used for the flavoring of cigarette, cigar and pipe tobaccos. Syrups, such as high fructose corn syrup, also can be employed. Certain flavoring agents may be incorporated within aerosol forming materials prior to formulation of a final aerosol precursor mixture (e.g., certain water soluble flavoring agents can be incorporated within water, menthol can be incorporated within propylene glycol, and certain complex flavor packages can be incorporated within propylene glycol).

Aerosol precursors also may include ingredients that exhibit acidic or basic characteristics (e.g., organic acids, ammonium salts or organic amines). For example, certain organic acids (e.g., levulinic acid, succinic acid, lactic acid, and pyruvic acid) may be included in an aerosol precursor formulation incorporating nicotine, preferably in amounts up to being equimolar (based on total organic acid content) with the nicotine. For example, the aerosol precursor may include about 0.1 to about 0.5 moles of levulinic acid per one mole of nicotine, about 0.1 to about 0.5 moles of succinic acid per one mole of nicotine, about 0.1 to about 0.5 moles of lactic acid per one mole of nicotine, about 0.1 to about 0.5 moles of pyruvic acid per one mole of nicotine, or various permutations and combinations thereof, up to a concentration wherein the total amount of organic acid present is equimolar to the total amount of nicotine present in the aerosol precursor.

As one non-limiting example, a representative aerosol precursor can have the form of a mixture of about 70% to about 90% glycerin, often about 75% to about 85% glycerin;

about 5% to about 20% water, often about 10% to about 15% water; about 1% to about 10% propylene glycol, often about 4% to about 8% propylene glycol; about 0.1% to about 6% nicotine, often about 1.5% to about 6% nicotine; and optional flavoring agent in an amount of up to about 6%, often about 0.1% to about 5% flavoring agent; on a weight basis. For example, a representative aerosol precursor may have the form of a formulation incorporating greater than about 76% glycerin, about 14% water, about 7% propylene glycol, about 1% to about 2% nicotine, and less than about 1% optional flavoring agent, on a weight basis. For example, a representative aerosol precursor may have the form of a formulation incorporating greater than about 75% glycerin, about 14% water, about 7% propylene glycol, about 2.5% nicotine, and less than about 1% optional flavoring agent. For example, a representative aerosol precursor may have the form of a formulation incorporating greater than about 75% glycerin, about 5% water, about 8% propylene glycol, about 6% nicotine, and less than about 6% optional flavoring agent, on a weight basis.

As another non-limiting example, a representative aerosol precursor can have the form of a mixture of about 40% to about 70% glycerin, often about 50% to about 65% glycerin; about 5% to about 20% water, often about 10% to about 15% water; about 20% to about 50% propylene glycol, often about 25% to about 45% propylene glycol; about 0.1% to about 6% nicotine, often about 1.5% to about 6% nicotine; about 0.5% to about 3%, often about 1.5% to about 2% menthol; and optional additional flavoring agent in an amount of up to about 6%, often about 0.1% to about 5% flavoring agent; on a weight basis. For example, a representative aerosol precursor may have the form of a formulation incorporating about 50% glycerin, about 11% water, about 28% propylene glycol, about 6% nicotine, about 2% menthol, and about 4% other flavoring agent, on a weight basis.

Representative types of aerosol precursor components and formulations also are set forth and characterized in U.S. Pat. No. 7,217,320 to Robinson et al. and U.S. Pat. Pub. Nos. 2013/0008457 to Zheng et al.; 2013/0213417 to Chong et al. and 2014/0060554 to Collett et al., the disclosures of which are incorporated herein by reference. Other aerosol precursors that may be employed include the aerosol precursors that have been incorporated in the VUSE® product by R. J. Reynolds Vapor Company, the BLU™ product by Lorillard Technologies, the MISTIC MENTHOL product by Mistic Ecigs, and the VYPE product by CN Creative Ltd. Also desirable are the so-called "smoke juices" for electronic cigarettes that have been available from Johnson Creek Enterprises LLC.

The amount of aerosol precursor that is incorporated within the aerosol delivery system is such that the aerosol generating piece provides acceptable sensory and desirable performance characteristics. For example, it is highly preferred that sufficient amounts of aerosol forming material (e.g., glycerin and/or propylene glycol), be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating piece. Typically, the amount of aerosol precursor incorporated within the aerosol delivery system, and particularly within the aerosol generating piece, is less than about 2 g, generally less than about 1.5 g, often less than about 1 g and frequently less than about 0.5 g.

The reservoir substrate 312 may be configured to absorb or otherwise retain the aerosol precursor composition directed into the reservoir compartment 376. However, in some instances the aerosol precursor composition may be directed into the reservoir compartment 376 at a fill rate that is greater than an absorptive rate of the reservoir substrate 312. Further, in some instances the amount of aerosol precursor composition directed into the reservoir compartment 376 may exceed the absorptive capacity of the reservoir substrate 312. Additionally, in some instances the aerosol precursor composition may absorb ambient moisture, causing the quantity of fluid in the reservoir compartment 376 to exceed the absorptive capacity of the reservoir substrate 312, even if the initially-filled quantity of the aerosol precursor composition did not exceed the absorptive capacity of the reservoir substrate.

However, despite the absorptive rate or absorptive capacity of the reservoir substrate 312 being exceeded, the aerosol precursor composition may still be retained in the reservoir compartment 376. In this regard, as discussed above, the seal between the outer body 314 and the flow director 308 may prevent leakage from the reservoir compartment 376. Accordingly, by employing the sealed reservoir compartment 376, issues with respect to exceeding the absorptive capacity of the cartridge 300 may be avoided, and the cartridge may be filled more quickly, which may expedite the cartridge assembly process.

Figure 13:
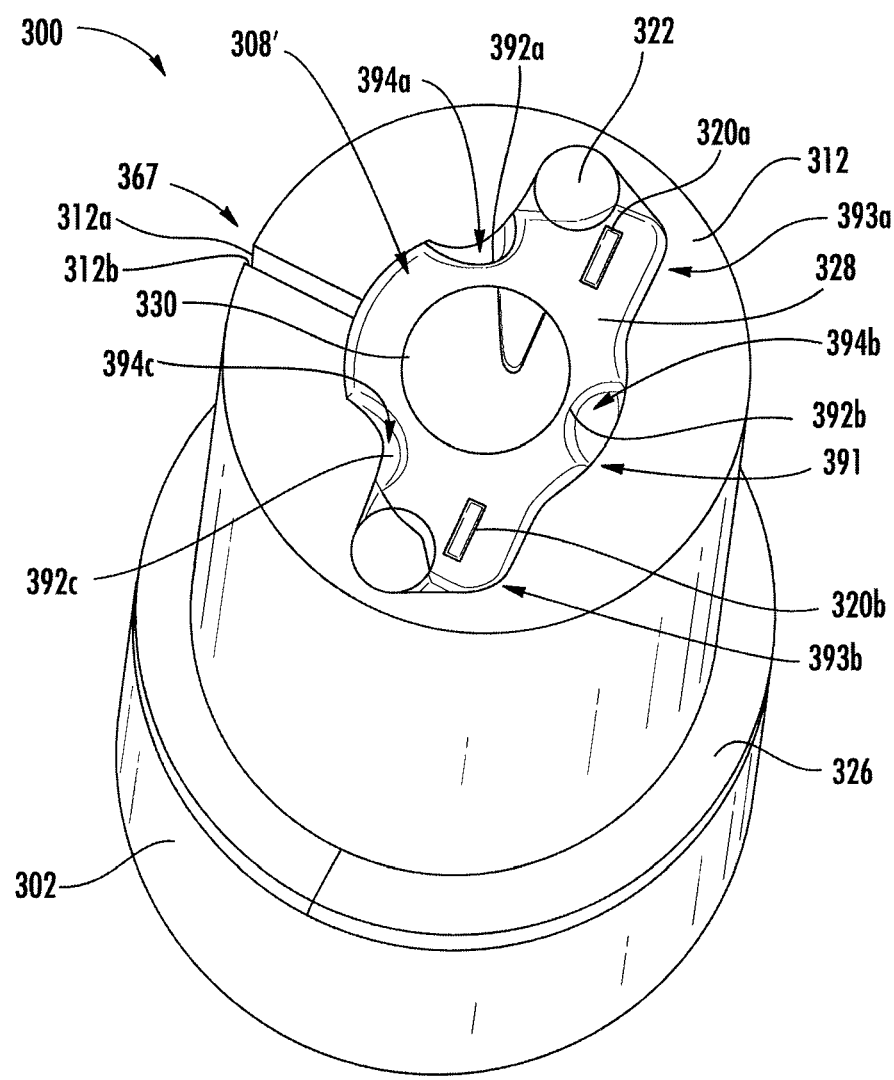

FIG. 13 illustrates a lateral sectional view through the partially assembled cartridge 300 along line 13-13 from FIG. 2 with the outer body 314 (see, e.g., FIG. 3) not shown for clarity purposes. In this regard, as may be understood, the outer body 314 may be attached prior to the filling process such that the aerosol precursor composition is retained in the reservoir compartment 376 (see, e.g., FIG. 3) during the filling process. As illustrated, one embodiment of the flow director 308' may define features configured to facilitate filling of the cartridge 300. In particular, the flow director 308' may define one or more recesses 392a-c.

In the illustrated embodiment the flow director 308' defines three recesses 392a-c. However additional or fewer recesses may be employed in other embodiments. The recesses 392a-c may each define a channel 394a-c between the flow director 308' and the reservoir substrate 312 configured to receive a filling device. For example, a filling needle or nozzle may be inserted into each channel 394a-c, or a nozzle may be directed into proximity to each channel, and an aerosol precursor composition may be directed into the channels. Accordingly, each channel 394a-c may facilitate rapid filling of the reservoir compartment 376 by allowing the channels 394a-c to initially fill up and then the reservoir substrate 312, which partially surrounds each channel, to absorb the aerosol precursor composition therefrom. When a filling needle or nozzle is directed into one of the channels 394a-c, the remaining channels may facilitate venting of air from around and in the reservoir substrate 312 displaced by the aerosol precursor composition to further facilitate rapid filling.

In embodiments in which the reservoir substrate 312 defines the gap 367 between the first and second ends 312a, 312b thereof, the gap may provide the same or similar functionality as the channels 394a-c. In this regard, a filling needle or nozzle may be inserted into the gap 367 to facilitate filling of the reservoir 312 with the aerosol precursor composition. Alternatively or additionally, the gap 367 may allow for venting of air from in and around the reservoir substrate 312 when the aerosol precursor composition is directed into contact with the reservoir substrate (e.g., when the aerosol precursor composition is directed into one of the channels 394a-c).

As further illustrated in FIG. 13, in some embodiments the flow director 308' may define a non-circular cross-section. For example, the flow director 308' may define, in cross-section, a core 391 and a plurality of lateral extensions or wings 393a, 393b protruding therefrom. The core 391 may be substantially tubular and the through hole 330 may extend therethrough. The above-described channels 394a-c may be defined in the core 391. Further, the wings 393a, 393b may extend from the core 391 so as to receive the heating terminals 320a, 320b therethrough.

Figure 14:
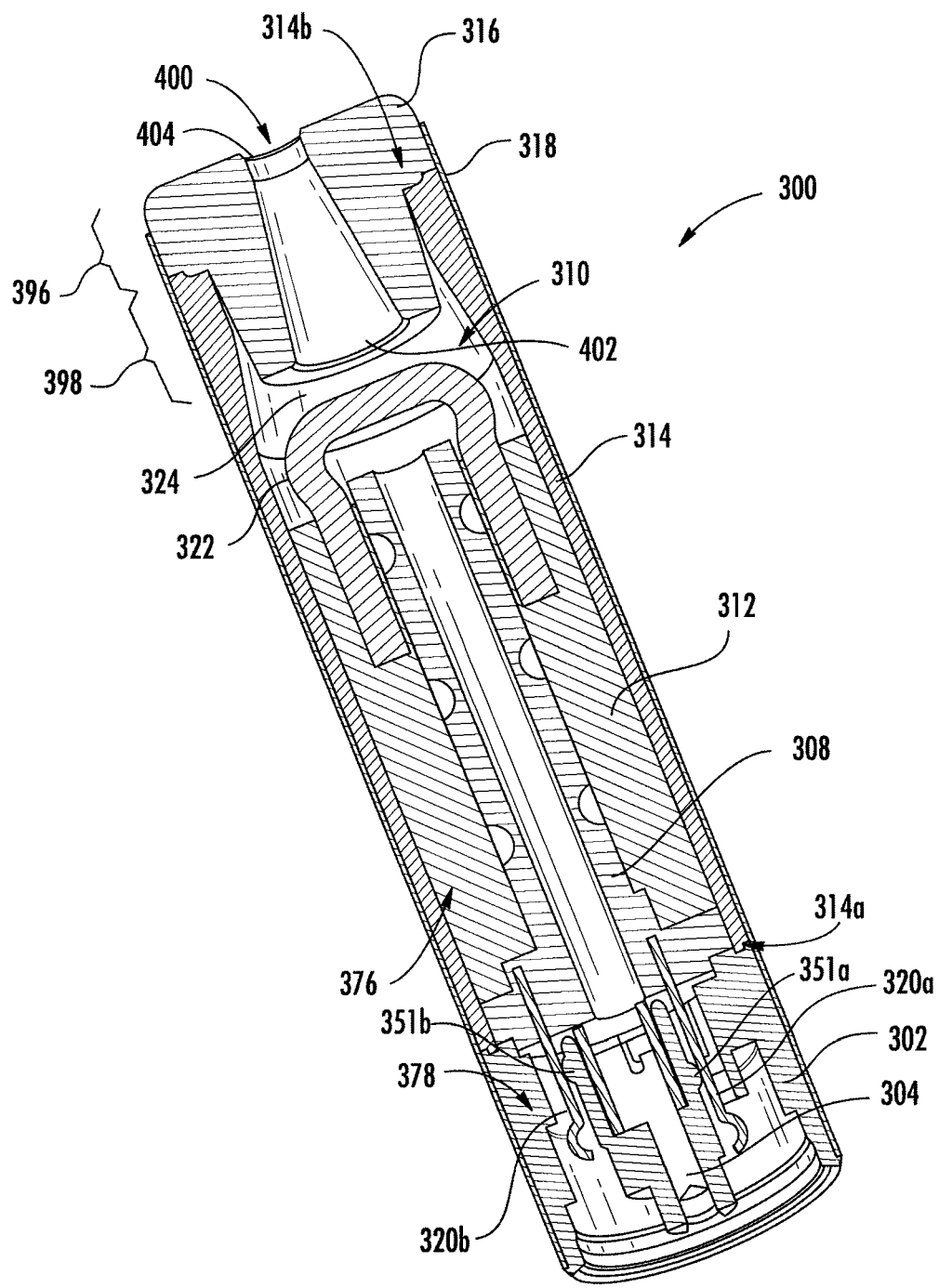

FIG. 14 illustrates a longitudinal cross-sectional view through the cartridge 300 in an assembled configuration along line 14-14 from FIG. 2. As illustrated, the mouthpiece 316 may couple to the outer body 314 at a second end 314b thereof, opposite from the base 302. Thereby, the mouthpiece 316 may at least partially enclose the reservoir compartment 376 at the second end 314b of the outer body 314. As further illustrated in FIG. 14, the label 318 may at least partially surround one or more of the outer body 314, the base 302, and the mouthpiece 316, for example, to provide the exterior of the cartridge 300 with a continuous, integral appearance. The label 318 may include an adhesive at an inner surface thereof or adhesive may otherwise be positioned between the label and the outer body 314, the base 302, and/or the mouthpiece 316.

In one embodiment the label 318 may comprise a single layer of a material (e.g., plastic, paper, or foil). Alternatively, the label 318 may comprise a multi-layer lamination (e.g., a lamination of plastic, paper, and/or foil). The label 318 may include indicia on an outer surface thereof. For example, the indicia may include information such as a product identifier, which may be formed by ink applied to one or more of the layers of the label 318. The indicia on the label 318 likewise may include texturing, coloring, and/or other physical attributes that may provide a desired appearance to the device, such as resembling a conventional cigarette or a conventional electronic cigarette. Example embodiments of labels which may be employed in the aerosol delivery device of the present disclosure are provided in U.S. Pat. Pub. No. 2013/0284190 to Scatterday et al., which is incorporated herein by reference in its entirety.

The mouthpiece 316 may be retained in engagement with the outer body 314 via a variety of mechanisms and methods. For example, the mouthpiece 316 may be secured to the outer body 314 via an adhesive, glue, sealant, or epoxy. In another embodiment the mouthpiece 316 may be welded (e.g., ultrasonically welded) to the outer body 314. Alternatively or additionally, the mouthpiece 316 may engage the outer body 314 via threaded engagement, interference fit, a crimp, or any other coupling mechanism.

As illustrated, the mouthpiece 316 may define an end portion 396 and an extension 398. The end portion 396 of the mouthpiece 316 may extend outwardly from the second end 314b of the outer body 314. Conversely, the extension 398 may extend into the outer body 314 such that the mouthpiece 316 is at least partially surrounded by the outer body.

The mouthpiece 316 may be configured to receive a draw from a user. In this regard, the mouthpiece 316 may define at least one aperture 400 through which air mixed with aerosol produced by the atomizer 310 may be directed when a user draws on the mouthpiece. In this regard, the aperture 400 may extend from an inlet 402 to an outlet 404. The inlet 402 may be configured to receive the aerosol generated by the atomizer 310 in the reservoir compartment 376. Conversely, the outlet 404 may be configured to deliver the aerosol to a user. In order to collect the aerosol generated by the atomizer 310, the inlet 402 to the aperture 400 may be relatively large. The outlet 404 to the aperture 400 may be smaller than the inlet 402 in order to provide a desired resistance to a draw on the mouthpiece 316 and substantially prevent access to the atomizer 310. For example, the inlet 402 may define a larger diameter than the outlet 404 in embodiments in which the inlet and outlet are round.

The extension 398 may be configured to reduce an empty volume within the outer body 314. In this regard, by reducing the empty volume (e.g., open space) in the outer body 314, the amount of air in the cartridge 300 may be reduced. Thereby, aerosol produced by the atomizer 310 may mix with less air prior to exiting through the mouthpiece 316. By reducing the quantity of air in the outer body 314 positioned between the atomizer 310 and the outlet 404 to the mouthpiece 316, the amount of aerosol precursor composition required to reach a given desired aerosol concentration exiting the mouthpiece 316 may be reduced. Thereby, for example, the cartridge 300 may produce a desired concentration of aerosol even in an instance in which a user makes a relatively small draw on the cartridge 300 and may reduce the quantity of any aerosol precursor composition wasted during such a small puff.

Further, as a result of the extension 398 decreasing the volume of open space in the cartridge 300, and in particular between the atomizer 310 and the outlet 404 to the aperture 400 through the mouthpiece 316, the quantity of aerosol remaining in the cartridge after a draw may be reduced. By reducing the amount of residual aerosol in the cartridge 300, less condensation may occur as the aerosol cools. As may be understood, such condensation may undesirably result in corrosion of metal parts (although any such metal parts may be selected and configured to avoid corrosion) or fluid leakage from the cartridge 300. Condensation remaining in the cartridge may also detrimentally affect the taste of the aerosol during future draws. Further, condensation may form deposits on the heating element 324 that may reduce the effectiveness thereof. Thereby, reducing the volume of empty space between the atomizer 310 and the outlet 404 to the aperture 400 through the mouthpiece 316 may provide additional benefits. The extension 398 may also improve a mechanical connection between the mouthpiece 316 and the outer body 314 by providing an elongated joint therebetween.

In some embodiments the mouthpiece 316 or a portion thereof may be deformable, consumable, and/or replaceable. For example, in some embodiments the extension 398 may be deformable, consumable, and/or replaceable. In this regard, some users may chew on the mouthpiece 316 during use of the aerosol delivery device 100. Thereby, use of a deformable material (e.g., a rubber material and/or cellulose acetate) may provide a user with a desired feel that mimics the feel of a filter of a traditional cigarette, for example. In some embodiments a tube may surround and support the aperture 400 such that the aperture does not become blocked in instances in which the mouthpiece 316 is deformed. Thereby, flow through the mouthpiece 316 may not be blocked when the user chews thereon. The mouthpiece 316 may define an elongated configuration external to the outer body 314 in some embodiments so as to facilitate chewing thereon. For example, the extension 398 may define a length about to about one inch in some embodiments.

Figure 15:
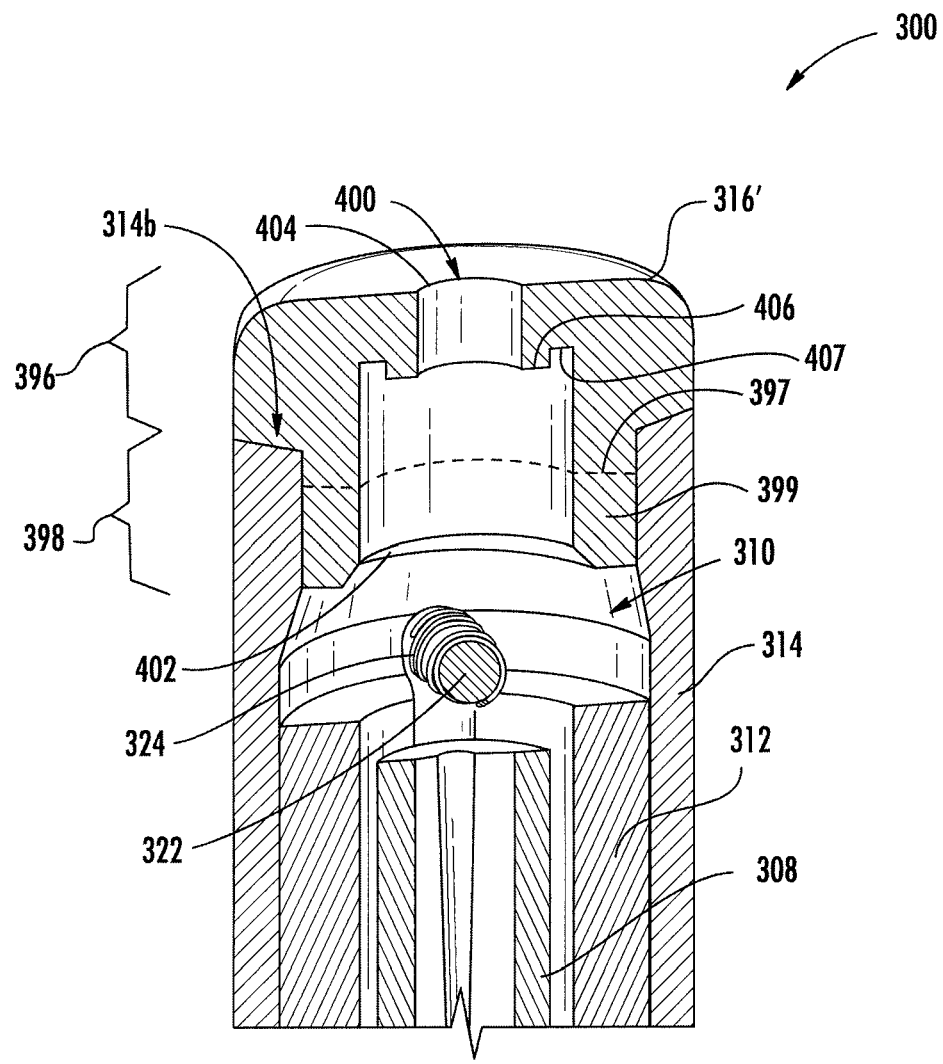

FIG. 15 illustrates a sectional view through the cartridge 300 along line 15-15 from FIG. 2 including an alternate embodiment of the mouthpiece 316'. As illustrated, the mouthpiece 316' includes the end portion 396 and the extension 398. Further, the mouthpiece 316' includes the aperture 400 extending therethrough between the inlet 402 and the outlet 404.

However, the mouthpiece 316' illustrated in FIG. 15 differs from the embodiment of the mouthpiece 316 illustrated in FIG. 14 in that the mouthpiece illustrated in FIG. 15 further comprises a lip 406 extending inwardly toward the atomizer 310 proximate the aperture 400. For example, as illustrated, the lip 406 may extend around the aperture 400 between the inlet 402 and the outlet 404. The lip 406 may define a bellmouth configured to reduce turbulence associated with flow of air and aerosol through the aperture 400 during a draw on the mouthpiece 316'. Accordingly, the amount of suction required to produce a desired airflow through the cartridge 300 during a draw on the mouthpiece 316' may be reduced by the lip 406, which may improve a user experience. The lip 406 may additionally or alternatively define a channel 407 extending around the aperture 400 and configured to capture small amounts of liquid (e.g., condensation), which may tend to form in proximity to the mouthpiece 316', as described above. In this regard, the lip 406 and the channel 407 may resist flow of any such liquid out of the aerosol delivery device through the aperture 400, which may otherwise undesirably leak out of the aerosol delivery device.

Although an extension of the mouthpiece was generally described above as reducing the volume of empty space within the cartridge between the atomizer and the outlet to the aperture through the mouthpiece, this volume of empty space may be reduced in additional or alternative manners. For example, a separate spacer may be inserted between the atomizer and the mouthpiece prior to coupling the mouthpiece to the outer body. In this regard, as further illustrated in FIG. 15, in one embodiment a spacer 397, which may comprise a separate component relative to the mouthpiece 316 (e.g, separated at the dashed lined 399), may be received in the outer body 314 between the mouthpiece and the atomizer 310.

Figure 16:
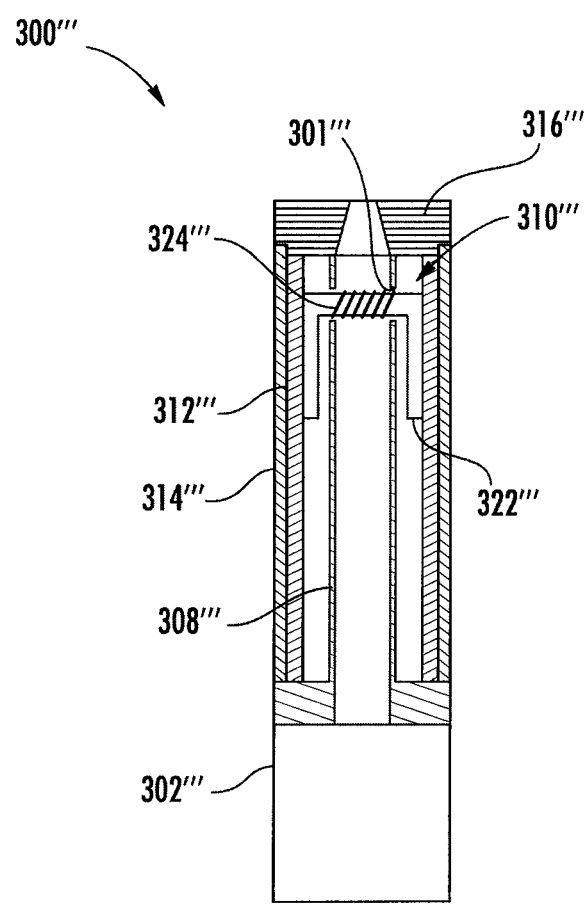

By way of further example, as illustrated in FIGS. 14 and 15, in one embodiment the outer body 314 may define an increased thickness proximate the mouthpiece 316 such that an internal diameter thereof is reduced. By way of further example, FIG. 16 schematically illustrates a modified sectional view through an alternate embodiment of a cartridge 300'''. The cartridge 300''' may include some or all of the above described components. In this regard, as illustrated, the cartridge 300''' may include a base 302''', a flow director 308''', an atomizer 310''' including a liquid transport element 322''' and a heating element 324''', a reservoir substrate 312''', an outer body 314''', and a mouthpiece 316'''. Note that certain components such as the heating terminals and label are not shown for clarity purposes.

However, as illustrated, a portion of the flow director 308''' may extend between the mouthpiece 316''' and the atomizer 310'''. For example, the atomizer 310''' may extend through a transverse aperture 301''' defined in the flow director 308'''. This configuration allows the reservoir substrate 312''' to be positioned between the atomizer 310''' and the mouthpiece 316''' (in terms of the longitudinal position thereof), which may provide the cartridge 300''' with an increased storage capacity for the aerosol precursor composition. In this regard, the flow director 308''' may separate the reservoir substrate 312 from contact with the atomizer 310'''. Further, by positioning the atomizer 310''' such that the heating element 324''' is separated from the reservoir substrate 312''' by the flow director 308''', issues with respect to the reservoir substrate migrating into contact with the heating element and/or being initially placed in contact with the heating element may be avoided.

As may be understood, alternate or additional configurations may be employed to reduce or eliminate empty space between the atomizer and the mouthpiece. For example, as described above, the outer body may protrude between the mouthpiece and the atomizer. However, regardless of the particular configuration employed, by reducing the empty space in the cartridge, and in particular the empty space between the atomizer and the mouthpiece, the cartridge may provide improved aerosol delivery to a user, reduce condensation in the cartridge, and/or provide as described above.

With reference, for example, to FIGS. 2 and 3, the cartridges 300 of the present disclosure may be employed with the control body 200 to produce aerosol. In this regard, during use a user may draw on the mouthpiece 316 of the cartridge 300 of the aerosol delivery device 100. This may pull air through an opening in the control body 200 or in the cartridge 300. For example, in one embodiment an opening may be defined between the coupler 202 and the outer body 204 of the control body 200, as described in U.S. patent application Ser. No. 13/841,233 to DePiano et al., filed Mar. 15, 2013, which is incorporated herein by reference in its entirety. However, the flow of air may be received through other parts of the aerosol delivery device 100 in other embodiments.

A sensor in the aerosol delivery device 100 such as the flow sensor 210 in the control body 200 may sense the puff. When the puff is sensed, the control body 200 may direct current to the heating element 324 from the electrical power source 216 through a circuit including the first heating terminal 320a and the second heating terminal 320b. Accordingly, the heating element 324 may vaporize the aerosol precursor composition directed to an aerosolization zone from the reservoir substrate 312 by the liquid transport element 322. Thus, the mouthpiece 316 may allow passage of air and entrained vapor (i.e., the components of the aerosol precursor composition in an inhalable form) from the cartridge 300 to a consumer drawing thereon. In particular, air may enter the cartridge from the coupler 202 through the third aperture 350c (see, e.g., FIG. 8) in the base 302 and travel through the through hole 330 in the flow director 308 past the atomizer 310 to the mouthpiece 326. Accordingly, the user may be provided with aerosol.

Figure 17:
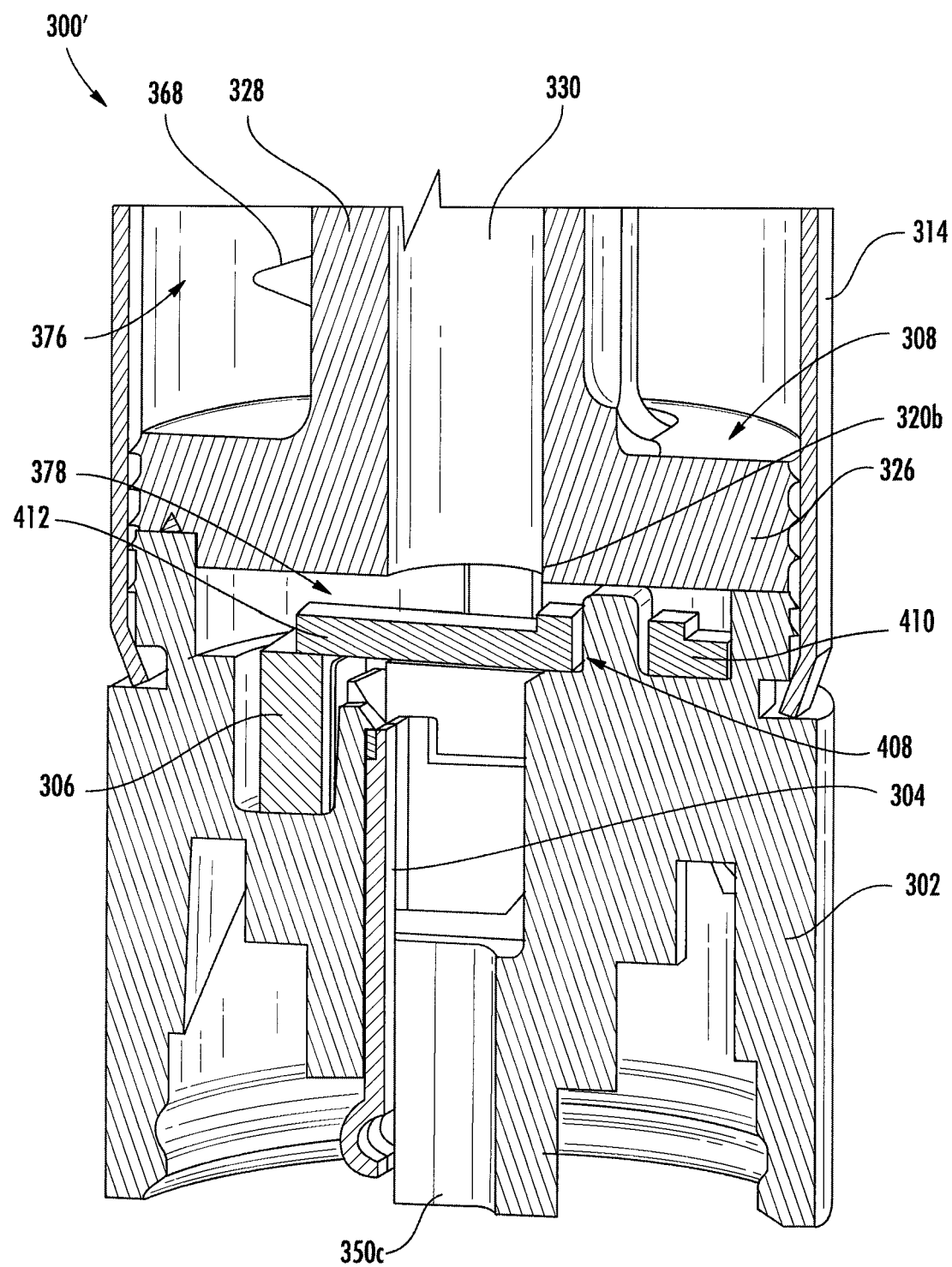

As noted above, the cartridges of the present disclosure may include a greater or lesser number of components in some embodiments. In this regard, FIG. 17 illustrates the cartridge 300' of FIG. 11 wherein the cartridge further comprises a one-way valve 408. The one-way valve 408 may be configured to resist flow of air from the flow director 308 through the base 302, which is opposite to the ordinary flow path therethrough. In other words, as described below, the one-way valve 408 is configured to resist a reverse puff received from the user and directed through the mouthpiece 316 to the flow director 308. As illustrated, the one-way valve 408 may include a retention portion 410 and a valve portion 412. The retention portion 412 may be configured to engage an adjacent portion of the cartridge 300' (e.g., part of the base 302) so as to retain the one-way valve 408 in place.

The valve portion 412 may be configured to allow flow through the cartridge 300' in one direction. In this regard, in the illustrated embodiment the one-way valve 408 is positioned in electronics compartment 378. Thereby, the valve portion 412 may extend into a flow path defined through the cartridge 300'.

The one-way valve 408 may comprise a flap valve in one embodiment. In this regard, the valve portion 412 may comprise a flap that at least partially blocks the third aperture 350c extending through the base 302 during certain situation. For example, the valve portion 412 may be configured to allow flow of air through the third aperture 350c in the base 302 to the through hole 330 through the flow director 308 when a user draws on the mouthpiece 316. However, in instances in which the user blows air into the mouthpiece 316, which may inadvertently or intentionally occur during use, flow of air through the through hole 330 through the flow director 308 and the base 302 may be resisted by the one-way valve 408. In this regard, the valve portion 412 may resist reverse flow through the third aperture 350c by coming into contact with the base 302, the electronic control component 306, the control component terminal 304 and/or any portion of a surrounding structure positioned proximate the third aperture 350c. In this regard, in some embodiments the valve portion 412 may press against such surrounding structure when there is no flow of air through the cartridge.

Figure 18:
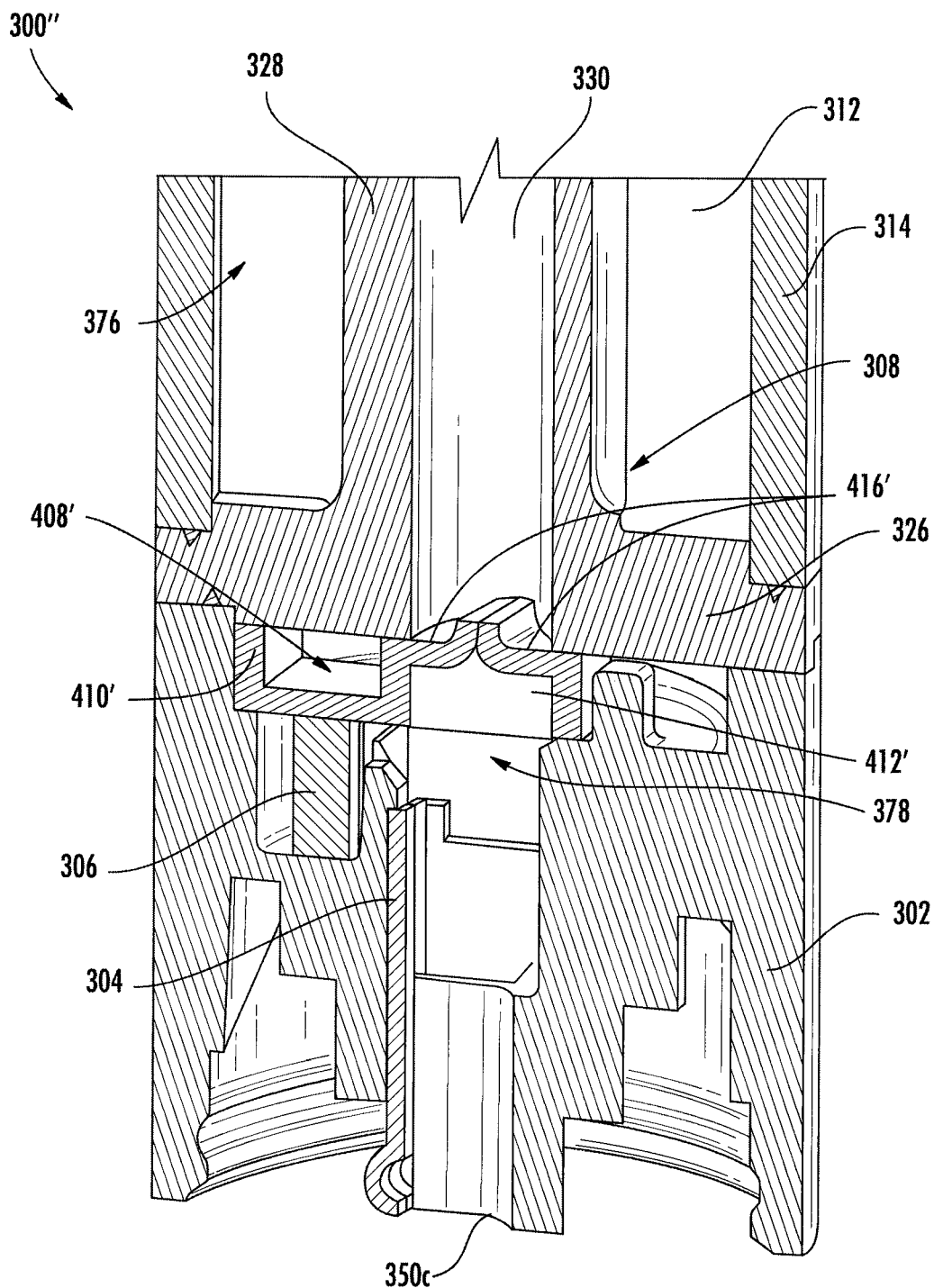

However, various other embodiments of one-way valves may be employed in accordance with the present disclosure. In this regard, FIG. 18 illustrates the cartridge 300" of FIG. 12 further comprising a second embodiment of a one-way valve 408'. As illustrated, the one-way valve 408' may be positioned in the electronics compartment 378. Further, the one-way valve 408' may comprise a retention portion 410' and a valve portion 412'. The one-way valve 408' illustrated in FIG. 18 differs from the one-way valve of FIG. 17 in that the one-way valve illustrated in FIG. 18 comprises a cross-valve. In this regard, the valve portion 412' of the one-way valve 408' may comprise a plurality of elastomeric members 416' that separate to allow flow therethrough from the third aperture 350c in the base 302 through the through hole 330 in the flow director 308 when a user draws on the mouthpiece 316. However, the elastomeric members 416' may press against one another when a user blows air into the mouthpiece 316 to substantially prevent flow of air through the through hole 330 through the flow director 308 and through the base 302. In this regard, in some embodiments the elastomeric members 416' may press against one another when there is no flow of air through the cartridge.

Accordingly, as described above, in some embodiments the one-way valves may comprise passive valves that respond to a user interaction with the cartridge to either allow or substantially prevent flow through the cartridge depending on whether a user is drawing on, or blowing into, the mouthpiece. However in other embodiments active one-way valves (e.g., solenoid valves) may be employed. Such active valves may act in substantially the same manner as described above based on the detected flow through the cartridge as controlled by a controller in the aerosol delivery device such as the electronic control component 306 or the control component 212 in the control body 200 (see, e.g., FIG. 2).

Further, although the one-way valves are generally described above as being positioned in the electronics compartment proximate the base, in other embodiments the one-way valve may be positioned in a different location. In this regard, the one-way valve may be positioned at any location along the flow path through the aerosol delivery device. Thus, by way of example, the one-way valve may be positioned at or near the mouthpiece, the flow director, the base, or even within the control body, such as at or near the coupler. Further, although use of one one-way valve is generally described herein, more than one one-way valve may be employed in other embodiments.

Figure 12:
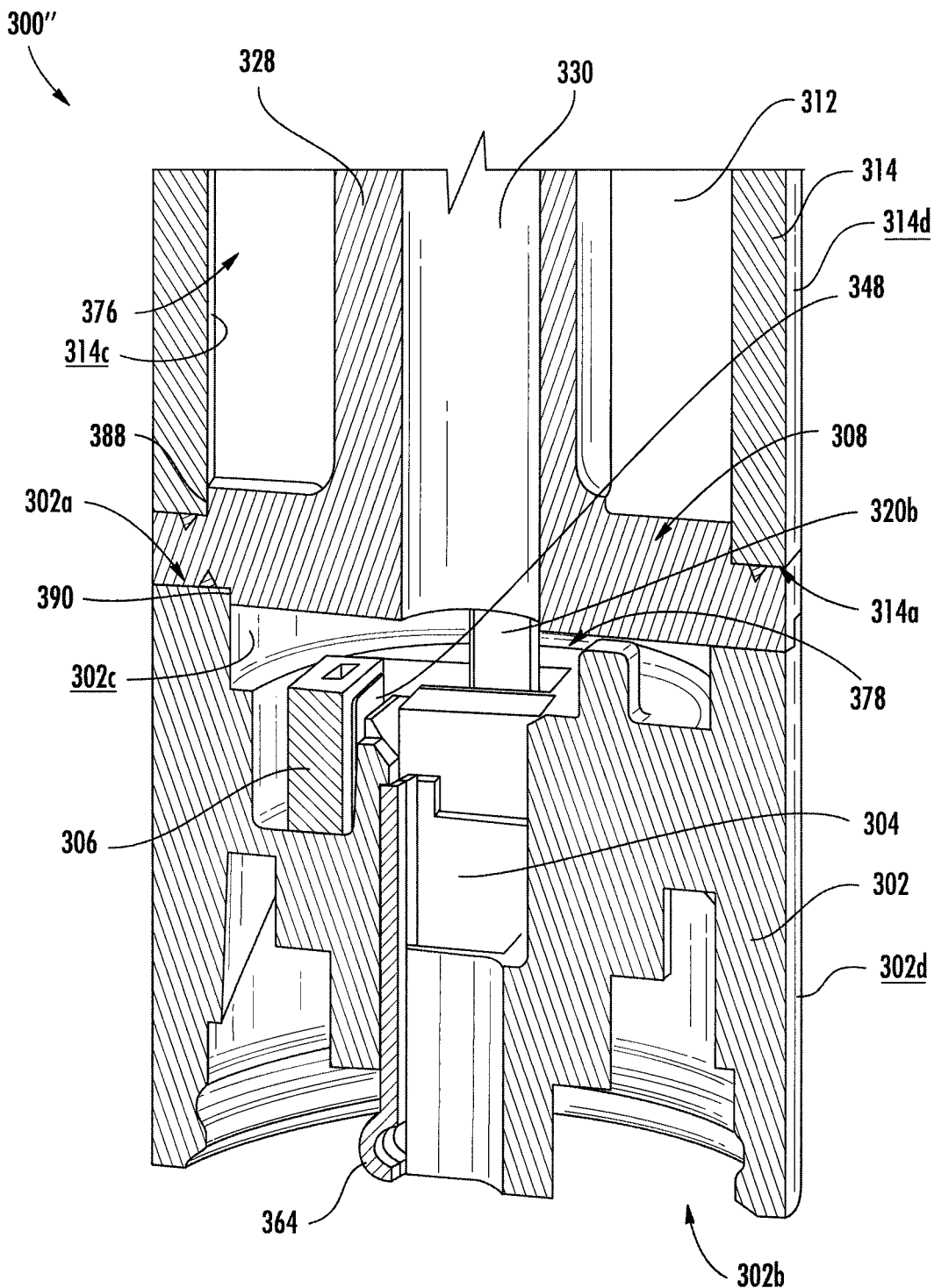

Various other details with respect to the components that may be included in the cartridge 300, are provided, for example, in U.S. patent application Ser. No. 13/840,264 to Novak, et al., filed Mar. 15, 2013, which is incorporated herein by reference in its entirety. In this regard, FIG. 7 thereof illustrates an enlarged exploded view of a base and a control component terminal; FIG. 8 thereof illustrates an enlarged perspective view of the base and the control component terminal in an assembled configuration; FIG. 9 thereof illustrates an enlarged perspective view of the base, the control component terminal, an electronic control component, and heating terminals of an atomizer in an assembled configuration; FIG. 10 thereof illustrates an enlarged perspective view of the base, the atomizer, and the control component in an assembled configuration; FIG. 11 thereof illustrates an opposing perspective view of the assembly of FIG. 10 thereof; FIG. 12 thereof illustrates an enlarged perspective view of the base, the atomizer, the flow director, and the reservoir substrate in an assembled configuration; FIG. 13 thereof illustrates a perspective view of the base and an outer body in an assembled configuration; FIG. 14 thereof illustrates a perspective view of a cartridge in an assembled configuration; FIG. 15 thereof illustrates a first partial perspective view of the cartridge of FIG. 14 thereof and a coupler for a control body; FIG. 16 thereof illustrates an opposing second partial perspective view of the cartridge of FIG. 14 thereof and the coupler of FIG. 11 thereof; FIG. 17 thereof illustrates a perspective view of a cartridge including a base with an anti-rotation mechanism; FIG. 18 thereof illustrates a perspective view of a control body including a coupler with an anti-rotation mechanism; FIG. 19 thereof illustrates alignment of the cartridge of FIG. 17 with the control body of FIG. 18; FIG. 3 thereof illustrates an aerosol delivery device comprising the cartridge of FIG. 17 thereof and the control body of FIG. 18 thereof with a modified view through the aerosol delivery device illustrating the engagement of the anti-rotation mechanism of the cartridge with the anti-rotation mechanism of the connector body; FIG. 4 thereof illustrates a perspective view of a base with an anti-rotation mechanism; FIG. 5 thereof illustrates a perspective view of a coupler with an anti-rotation mechanism; and FIG. 6 thereof illustrates a sectional view through the base of FIG. 4 thereof and the coupler of FIG. 5 thereof in an engaged configuration.

A method for assembling a cartridge for an aerosol delivery device is also provided. As illustrated in FIG. 19, the method may include coupling a base to a flow director such that the flow director and the base define an electronics compartment at operation 502. Further, the method may include positioning an atomizer within an outer body at operation 504. The method may additionally include coupling the outer body to the flow director such that the outer body and the flow director define a reservoir compartment at operation 506.

In some embodiments the method may further comprise wrapping a reservoir substrate configured to store an aerosol precursor composition at least partially about the flow director. The method may additionally include positioning the reservoir substrate within the reservoir compartment, which may occur during positioning the atomizer within the outer body at operation 504.

In some embodiments wrapping the reservoir substrate at least partially about the flow director may include engaging the reservoir substrate with a plurality of protrusions defined by the flow director and extending therefrom. In another embodiment wrapping the reservoir substrate at least partially about the flow director may include wrapping the reservoir substrate partially about the flow director such that a gap is defined between first and second ends thereof. In an additional embodiment wrapping the reservoir substrate at least partially about the flow director may comprise forming a channel between the flow director and the reservoir substrate at a cutout defined in the flow director. The method may additionally include filling the reservoir substrate with the aerosol precursor composition by directing the aerosol precursor composition into at least one of a gap between first and second ends of the reservoir substrate and a channel between the flow director and the reservoir substrate at a cutout defined in the flow director.

The method may further include molding at least one heating terminal into the flow director. Additionally, the method may include positioning an electronic control component in the electronics compartment and connecting a control component terminal to the electronic control component. Further, coupling the outer body to the flow director at operation 506 may comprise deforming a deformable rib of the flow director against an inner surface of the outer body. In another embodiment coupling the outer body to the flow director at operation 506 may comprise welding the outer body to the flow director.

The method may additionally include coupling the outer body to the base. Coupling the outer body to the base may comprise deforming a deformable rib of the base against an inner surface of the outer body. Further, coupling the base to the flow director at operation 502 may comprise welding the base to the flow director. Additionally, the method may include coupling a one-way valve to the base. The one-way valve may be configured to resist flow of air from the flow director through the base.

In an additional embodiment a controller is provided. The controller may be configured to execute computer code for performing the operations described herein. In this regard, as illustrated in FIG. 20, the controller 600 may comprise a processor 602 that may be a microprocessor or a controller for controlling the overall operation thereof. In one embodiment the processor 602 may be particularly configured to execute program code instructions related to the functions described herein, including the operations for assembling the cartridge 300 of the present disclosure. The controller 600 may also include a memory device 604. The memory device 604 may include non-transitory and tangible memory that may be, for example, volatile and/or non-volatile memory. The memory device 604 may be configured to store information, data, files, applications, instructions or the like. For example, the memory device 604 could be configured to buffer input data for processing by the processor 602. Additionally or alternatively, the memory device 604 may be configured to store instructions for execution by the processor 602.

The controller 600 may also include a user interface 606 that allows a user to interact therewith. For example, the user interface 606 can take a variety of forms, such as a button, keypad, dial, touch screen, audio input interface, visual/image capture input interface, input in the form of sensor data, etc. Still further, the user interface 606 may be configured to output information to the user through a display, speaker, or other output device. A communication interface 608 may provide for transmitting and receiving data through, for example, a wired or wireless network 610 such as a local area network (LAN), a metropolitan area network (MAN), and/or a wide area network (WAN), for example, the Internet. The communication interface 608 may enable the controller 600 to communicate with one or more further computing devices, either directly, or via the network 610. In this regard, the communication interface 608 may include one or more interface mechanisms for enabling communication with other devices and/or networks. The communication interface 608 may accordingly include one or more interface mechanisms, such as an antenna (or multiple antennas) and supporting hardware and/or software for enabling communications via wireless communication technology (e.g., a cellular technology, communication technology, Wi-Fi and/or other IEEE 802.11 technology, Bluetooth, Zigbee, wireless USB, NFC, RF-ID, WiMAX and/or other IEEE 802.16 technology, and/or other wireless communication technology) and/or a communication modem or other hardware/software for supporting communication via cable, digital subscriber line (DSL), USB, FireWire, Ethernet, one or more optical transmission technologies, and/or other wireline networking methods. Further, the controller 600 may include an assembly module 612. The assembly module 612 may be configured to, in conjunction with the processor 602, direct operations for assembling a cartridge as described herein.

The various aspects, embodiments, implementations or features of the described embodiments can be used separately or in any combination. Various aspects of the described embodiments can be implemented by software, hardware or a combination of hardware and software. The described embodiments can also be embodied as computer readable code on a computer readable medium for controlling the above-described operations. In particular, computer readable code may be configured to perform each of the operations of the methods described herein and embodied as computer readable code on a computer readable medium for controlling the above-described operations. In this regard, a computer readable storage medium, as used herein, refers to a non-transitory, physical storage medium (e.g., a volatile or non-volatile memory device, which can be read by a computer system. Examples of the computer readable medium include read-only memory, random-access memory, CD-ROMs, DVDs, magnetic tape, and optical data storage devices. The computer readable medium can also be distributed over network-coupled computer systems so that the computer readable code is stored and executed in a distributed fashion.

As noted above, the controller 600 may be configured to execute computer code for performing the above-described assembly operations. In this regard, an embodiment of a non-transitory computer readable medium for storing computer instructions executed by a processor in a controller (e.g. controller 600) configured to assemble a cartridge for an aerosol delivery device is provided. The non-transitory computer readable medium may comprise program code instructions for coupling a base to a flow director such that the flow director and the base define an electronics compartment, program code instructions for positioning an atomizer within an outer body; and program code instructions for coupling the outer body to the flow director such that the outer body and the flow director define a reservoir compartment.

In some embodiments the computer readable medium may further comprise program code instructions for wrapping a reservoir substrate configured to store an aerosol precursor composition at least partially about the flow director such that the reservoir substrate engages a plurality of protrusions defined by the flow director and extending therefrom and program code instructions for positioning the reservoir substrate within the reservoir compartment. The program code instructions for wrapping the reservoir substrate at least partially about the flow director may comprise program code instructions for forming a channel between the flow director and the reservoir substrate at a cutout defined in the flow director.

In some embodiments the computer readable medium may further comprise program code instructions for molding at least one heating terminal into the flow director. The computer readable medium may further comprise program code instructions for positioning an electronic control component in the electronics compartment and program code instructions for connecting a control component terminal to the electronic control component. The program code instructions for coupling the outer body to the flow director may comprise program code instructions for deforming a deformable rib of the flow director against an inner surface of the outer body. The program code instructions for coupling the outer body to the flow director may comprise program code instructions for welding the outer body to the flow director.

In some embodiments the computer readable medium may further comprise program code instructions for coupling the outer body to the base, wherein the program code instructions for coupling the outer body to the base comprise program code instructions for deforming a deformable rib of the base against an inner surface of the outer body. Further, the program code instructions for coupling the base to the flow director may comprise program code instructions for welding the base to the flow director. In some embodiments the computer readable medium may further comprise program code instructions for coupling a one-way valve to the base, the one-way valve being configured to resist flow of air from the flow director through the base.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. A cartridge for an aerosol delivery device, comprising:
   an outer body defining an engaging end configured to engage a control body and an opposing mouth end;
   a mouthpiece coupled to the mouth end of the outer body, the mouthpiece defining an elongate configuration external to the outer body;

a base disposed proximate the engaging end;

an aerosolization zone defined within the outer body;

a reservoir defined within the outer body and spaced apart from the aerosolization zone, the reservoir containing an aerosol precursor composition;

a heating element positioned within the aerosolization zone, the heating element comprising a wire defining a plurality of coils;

a liquid transport element configured to transfer the aerosol precursor composition from the reservoir to the heating element;

a first heating terminal extending into the outer body such that a first tab of the first heating terminal is positioned adjacent to and in direct contact with a portion of the wire defining the plurality of coils and such that a first end of the first heating terminal extends out of the base and is configured to engage a first electrical contact of a control body; and a second heating terminal extending into the outer body such that a second tab of the second heating terminal is positioned adjacent to and in direct contact with a portion of the wire defining the plurality of coils and such that a second end of the second heating terminal extends out of the base and is configured to engage a second electrical contact of the control body, wherein the first end of the first heating terminal and the second end of the second heating terminal are each at least partially bent at an angle relative to the base so as to provide for a secure engagement of the first end of the first heating terminal and the second end of the second heating terminal with the first electrical contact and the second electrical contact of the control body.

2. The cartridge of claim 1, wherein the outer body comprises a non-circular cross-section.

3. The cartridge of claim 2, wherein the outer body comprises at least one planar surface.

4. The cartridge of claim 1, wherein the liquid transport element is at least partially positioned outside of the reservoir containing the aerosol precursor composition, but still in fluid connection with the aerosol precursor composition.

5. The cartridge of claim 1, wherein the heating element is in direct contact with the liquid transport element so as to directly apply heat thereto.

6. The cartridge of claim 1, wherein the control body includes one or more control components that actuate or regulate flow of an electrical current from an electrical power source.

7. The cartridge of claim 6, wherein the one or more control components are configured to permit current flow through the heating element for up to a defined period of time during application of suction to an opening in the mouthpiece.

8. The cartridge of claim 1, wherein the heating element comprises a resistive heating element.

9. The cartridge of claim 6, wherein the electrical power source is rechargeable via a USB connection.

10. The cartridge of claim 1, wherein the control body includes one or more indicators of active use of the aerosol delivery device.

11. The cartridge of claim 1, wherein the control body includes one or more control components configured to:

determine engagement of the cartridge with the control body; and perform a function in response to engagement of the cartridge with the control body.

12. The cartridge of claim 11, wherein the one or more control components are configured to determine a property of the cartridge in response to engagement of the cartridge with the control body.

13. The cartridge of claim 11, wherein the one or more control components are configured to cause illumination of an indicator light in response to engagement of the cartridge with the control body.

14. The cartridge of claim 1, wherein the control body comprises a power source, wherein when the engaging end of the outer body of the cartridge is brought into press-fit engagement with the control body, the first and second electrical contacts of the control body engage the first and second heating terminals of the outer body of the cartridge so as to electrically couple the heating element with the power source.

15. The cartridge of claim 1, wherein the first and second heater terminals extend through the base so that the bent first and second ends are exposed relative to the outer body of the cartridge.

16. The cartridge of claim 1, wherein the mouthpiece is coupled to the mouth end of the outer body via engagement of corresponding protrusions and indentations.

17. The cartridge of claim 1, wherein the first end of the first heating terminal and the second end of the second heating terminal are each bent from opposite peripheral sections of the base toward a central section of the base.

18. The cartridge of claim 1, wherein the first end of the first heating terminal and the second end of the second heating terminal comprise a spring bias so as to securely engage respective ones of the first electrical contact and the second electrical contact of the control body.

* * * * *